(12) United States Patent
Olmos et al.

(10) Patent No.: US 8,568,481 B2
(45) Date of Patent: Oct. 29, 2013

(54) INTERVERTEBRAL IMPLANT

(75) Inventors: Fausto Olmos, Laguna Niguel, CA (US); Brad Culbert, Rancho Santa Margarita, CA (US); Bob Flower, Sun City, CA (US)

(73) Assignee: Interventional Spine, Inc., Irvine, CA (US)

( * ) Notice: Subject to any disclaimer, the term of this patent is extended or adjusted under 35 U.S.C. 154(b) by 17 days.

(21) Appl. No.: 13/334,526

(22) Filed: Dec. 22, 2011

(65) Prior Publication Data
US 2012/0191194 A1    Jul. 26, 2012

Related U.S. Application Data

(63) Continuation of application No. 11/952,900, filed on Dec. 7, 2007, now Pat. No. 8,105,382.

(60) Provisional application No. 60/869,088, filed on Dec. 7, 2006.

(51) Int. Cl.
*A61F 2/44* (2006.01)

(52) U.S. Cl.
USPC ...................................... 623/17.15

(58) Field of Classification Search
USPC ........................... 623/17.11–17.16
See application file for complete search history.

(56) References Cited

U.S. PATENT DOCUMENTS

| | | |
|---|---|---|
| 4,401,112 A | 8/1983 | Rezaian |
| 4,863,476 A | 9/1989 | Shepperd |
| 5,171,278 A | 12/1992 | Pisharodi |
| 5,171,280 A | 12/1992 | Baumgartner |
| 5,308,327 A | 5/1994 | Heaven et al. |
| 5,344,252 A | 9/1994 | Kakimoto |
| 5,390,683 A | 2/1995 | Pisharodi |
| 5,424,773 A | 6/1995 | Saito |
| 5,514,180 A | 5/1996 | Heggeness et al. |
| 5,554,191 A | 9/1996 | Lahille et al. |
| 5,653,763 A | 8/1997 | Errico et al. |

(Continued)

FOREIGN PATENT DOCUMENTS

| | | |
|---|---|---|
| DE | 3 023 353 | 4/1981 |
| EP | 0 077 159 | 4/1983 |

(Continued)

OTHER PUBLICATIONS

Preliminary Report on Patentability received in co-pending PCT application No. PCT/US2007/086866, mailed Jun. 18, 2009, in 7 pages.

(Continued)

*Primary Examiner* — Bruce E Snow
(74) *Attorney, Agent, or Firm* — Knobbe, Martens, Olson & Bear LLP

(57) ABSTRACT

An adjustable spinal fusion intervertebral implant is provided that can comprise upper and lower body portions that can each have proximal and distal wedge surfaces disposed at proximal and distal ends thereof. An actuator shaft disposed intermediate the upper and lower body portions can be actuated to cause proximal and distal protrusions to converge towards each other and contact the respective ones of the proximal and distal wedge surfaces. Such contact can thereby transfer the longitudinal movement of the proximal and distal protrusions against the proximal and distal wedge surfaces to cause the separation of the upper and lower body portions, thereby expanding the intervertebral implant.

9 Claims, 28 Drawing Sheets

(56) References Cited

U.S. PATENT DOCUMENTS

| | | | |
|---|---|---|---|
| 5,658,335 A * | 8/1997 | Allen | 623/17.16 |
| 5,665,122 A | 9/1997 | Kambin | |
| 5,693,100 A | 12/1997 | Pisharodi | |
| 5,702,391 A | 12/1997 | Lin | |
| 5,716,416 A | 2/1998 | Lin | |
| 5,762,500 A | 6/1998 | Lazarof | |
| 5,865,848 A | 2/1999 | Baker | |
| 5,893,889 A | 4/1999 | Harrington | |
| 5,976,186 A | 11/1999 | Bao et al. | |
| 5,980,522 A | 11/1999 | Koros et al. | |
| 6,080,193 A | 6/2000 | Hochshuler et al. | |
| 6,102,950 A | 8/2000 | Vaccaro | |
| 6,129,763 A | 10/2000 | Chauvin et al. | |
| 6,168,597 B1 | 1/2001 | Biedermann et al. | |
| 6,176,882 B1 * | 1/2001 | Biedermann et al. | 623/17.15 |
| 6,245,107 B1 | 6/2001 | Ferree | |
| 6,368,351 B1 | 4/2002 | Glenn et al. | |
| 6,375,682 B1 | 4/2002 | Fleischmann et al. | |
| 6,387,130 B1 | 5/2002 | Stone et al. | |
| 6,419,704 B1 | 7/2002 | Ferree | |
| 6,425,919 B1 | 7/2002 | Lambrecht | |
| 6,436,143 B1 | 8/2002 | Ross et al. | |
| 6,443,989 B1 | 9/2002 | Jackson | |
| 6,454,807 B1 | 9/2002 | Jackson | |
| 6,468,310 B1 | 10/2002 | Ralph et al. | |
| 6,562,074 B2 | 5/2003 | Gerbec et al. | |
| 6,576,016 B1 | 6/2003 | Hochshuler et al. | |
| 6,595,998 B2 | 7/2003 | Johnson et al. | |
| 6,620,196 B1 | 9/2003 | Trieu | |
| 6,685,742 B1 | 2/2004 | Jackson | |
| 6,716,247 B2 | 4/2004 | Michelson | |
| 6,723,126 B1 | 4/2004 | Berry | |
| 6,730,126 B2 | 5/2004 | Boehm, Jr. et al. | |
| 6,733,535 B2 | 5/2004 | Michelson | |
| 6,733,635 B1 | 5/2004 | Ozawa et al. | |
| 6,740,093 B2 | 5/2004 | Hochschuler et al. | |
| 6,773,460 B2 | 8/2004 | Jackson | |
| 6,805,695 B2 | 10/2004 | Keith | |
| 6,808,537 B2 | 10/2004 | Michelson | |
| 6,821,298 B1 | 11/2004 | Jackson | |
| 6,830,589 B2 | 12/2004 | Erickson | |
| 6,835,206 B2 | 12/2004 | Jackson | |
| 6,893,466 B2 | 5/2005 | Trieu | |
| 6,936,072 B2 | 8/2005 | Lambrecht et al. | |
| 6,972,035 B2 | 12/2005 | Michelson | |
| 6,997,929 B2 | 2/2006 | Manzi et al. | |
| 7,004,945 B2 | 2/2006 | Boyd et al. | |
| 7,018,415 B1 | 3/2006 | McKay | |
| 7,066,961 B2 | 6/2006 | Michelson | |
| 7,094,257 B2 | 8/2006 | Mujwid et al. | |
| 7,094,258 B2 | 8/2006 | Lambrecht et al. | |
| 7,114,501 B2 | 10/2006 | Johnson et al. | |
| 7,118,579 B2 | 10/2006 | Michelson | |
| 7,118,598 B2 | 10/2006 | Michelson | |
| 7,128,760 B2 | 10/2006 | Michelson | |
| 7,153,305 B2 | 12/2006 | Johnson et al. | |
| 7,179,294 B2 | 2/2007 | Eisermann et al. | |
| 7,306,628 B2 | 12/2007 | Zucherman et al. | |
| 7,309,357 B2 | 12/2007 | Kim | |
| 7,410,501 B2 | 8/2008 | Michelson | |
| 7,445,636 B2 | 11/2008 | Michelson | |
| D626,233 S | 10/2010 | Cipoletti et al. | |
| 7,819,921 B2 | 10/2010 | Grotz | |
| 7,837,734 B2 | 11/2010 | Flynn | |
| 7,850,733 B2 | 12/2010 | Baynham et al. | |
| 8,062,375 B2 | 11/2011 | Glerum | |
| 8,133,232 B2 | 3/2012 | Levy | |
| 8,262,736 B2 | 9/2012 | Michelson | |
| 8,273,129 B2 | 9/2012 | Baynham et al. | |
| 8,317,866 B2 | 11/2012 | Palmatier | |
| 8,366,777 B2 | 2/2013 | Matthis et al. | |
| 8,398,713 B2 | 3/2013 | Weiman | |
| 2002/0183848 A1 | 12/2002 | Ray et al. | |
| 2003/0065396 A1 * | 4/2003 | Michelson | 623/17.15 |
| 2004/0024463 A1 | 2/2004 | Thomas | |
| 2004/0097924 A1 | 5/2004 | Lambrecht et al. | |
| 2004/0133280 A1 | 7/2004 | Trieu | |
| 2004/0153156 A1 * | 8/2004 | Cohen et al. | 623/17.13 |
| 2004/0172134 A1 | 9/2004 | Berry | |
| 2004/0186471 A1 | 9/2004 | Trieu | |
| 2004/0215343 A1 | 10/2004 | Hochschuler et al. | |
| 2004/0215344 A1 | 10/2004 | Hochschuler et al. | |
| 2004/0220580 A1 | 11/2004 | Johnson | |
| 2004/0225361 A1 | 11/2004 | Glenn et al. | |
| 2005/0043796 A1 | 2/2005 | Grant et al. | |
| 2005/0065610 A1 | 3/2005 | Pisharodi | |
| 2005/0102202 A1 | 5/2005 | Linden et al. | |
| 2005/0130929 A1 | 6/2005 | Boyd | |
| 2005/0131406 A1 | 6/2005 | Reiley et al. | |
| 2005/0171552 A1 | 8/2005 | Johnson et al. | |
| 2005/0182414 A1 | 8/2005 | Manzi et al. | |
| 2005/0182418 A1 | 8/2005 | Boyd et al. | |
| 2005/0187558 A1 | 8/2005 | Johnson et al. | |
| 2005/0187559 A1 | 8/2005 | Raymond et al. | |
| 2005/0278026 A1 | 12/2005 | Gordon et al. | |
| 2006/0004326 A1 | 1/2006 | Collins et al. | |
| 2006/0004457 A1 | 1/2006 | Collins et al. | |
| 2006/0004458 A1 | 1/2006 | Collins et al. | |
| 2006/0009778 A1 | 1/2006 | Collins et al. | |
| 2006/0009779 A1 | 1/2006 | Collins et al. | |
| 2006/0009851 A1 | 1/2006 | Collins et al. | |
| 2006/0041314 A1 | 2/2006 | Millard | |
| 2006/0058807 A1 | 3/2006 | Landry et al. | |
| 2006/0058880 A1 | 3/2006 | Wysocki et al. | |
| 2006/0119629 A1 | 6/2006 | An et al. | |
| 2006/0129244 A1 | 6/2006 | Ensign | |
| 2006/0161166 A1 | 7/2006 | Johnson et al. | |
| 2006/0178743 A1 | 8/2006 | Carter | |
| 2006/0276899 A1 | 12/2006 | Zipnick | |
| 2006/0276901 A1 | 12/2006 | Zipnick | |
| 2006/0276902 A1 | 12/2006 | Zipnick | |
| 2006/0293663 A1 | 12/2006 | Walkenhorst et al. | |
| 2007/0010826 A1 | 1/2007 | Rhoda | |
| 2007/0032790 A1 | 2/2007 | Aschmann et al. | |
| 2007/0067035 A1 | 3/2007 | Falahee | |
| 2007/0073399 A1 | 3/2007 | Zipnick | |
| 2007/0118223 A1 | 5/2007 | Allard et al. | |
| 2007/0129730 A1 | 6/2007 | Woods et al. | |
| 2007/0203491 A1 | 8/2007 | Pasquet et al. | |
| 2007/0270968 A1 | 11/2007 | Baynham et al. | |
| 2007/0282449 A1 | 12/2007 | de Villiers | |
| 2009/0222100 A1 | 9/2009 | Cipoletti et al. | |
| 2010/0082109 A1 | 4/2010 | Greenhalgh | |
| 2010/0191336 A1 | 7/2010 | Greenhalgh | |
| 2010/0211176 A1 | 8/2010 | Greenhalgh | |
| 2011/0153020 A1 | 6/2011 | Abdelgany | |
| 2011/0172774 A1 | 7/2011 | Varela | |
| 2011/0238072 A1 | 9/2011 | Tyndall | |
| 2011/0282453 A1 | 11/2011 | Greenhalgh | |
| 2012/0059474 A1 | 3/2012 | Weiman | |
| 2012/0059475 A1 | 3/2012 | Weiman | |
| 2012/0150304 A1 | 6/2012 | Glerum | |
| 2012/0150305 A1 | 6/2012 | Glerum | |
| 2012/0158146 A1 | 6/2012 | Glerum | |
| 2012/0158147 A1 | 6/2012 | Glerum | |
| 2012/0158148 A1 | 6/2012 | Glerum | |
| 2012/0185049 A1 | 7/2012 | Varela | |
| 2012/0197405 A1 | 8/2012 | Cuevas | |
| 2012/0203347 A1 | 8/2012 | Glerum | |
| 2012/0226357 A1 | 9/2012 | Varela | |
| 2012/0265309 A1 | 10/2012 | Glerum | |
| 2012/0290090 A1 | 11/2012 | Glerum | |
| 2012/0290097 A1 | 11/2012 | Cipoletti | |
| 2012/0323328 A1 | 12/2012 | Weiman | |
| 2012/0330421 A1 | 12/2012 | Weiman | |
| 2012/0330422 A1 | 12/2012 | Weiman | |
| 2013/0006361 A1 | 1/2013 | Glerum | |
| 2013/0023993 A1 | 1/2013 | Weiman | |
| 2013/0023994 A1 | 1/2013 | Glerum | |

FOREIGN PATENT DOCUMENTS

| | | |
|---|---|---|
| EP | 0260044 | 3/1988 |
| WO | WO 2006/067652 | 5/2000 |

(56) References Cited

FOREIGN PATENT DOCUMENTS

| | | |
|---|---|---|
| WO | WO 2008/070863 | 6/2008 |
| WO | WO 2010/148112 A1 | 12/2010 |
| WO | WO 2011/142761 A1 | 11/2011 |
| WO | WO 2011/150350 A1 | 12/2011 |

OTHER PUBLICATIONS

International Search Report and Written Opinion received in co-pending PCT application No. PCT/US2007/086866, mailed Jul. 7, 2008, 11 pages.

\* cited by examiner

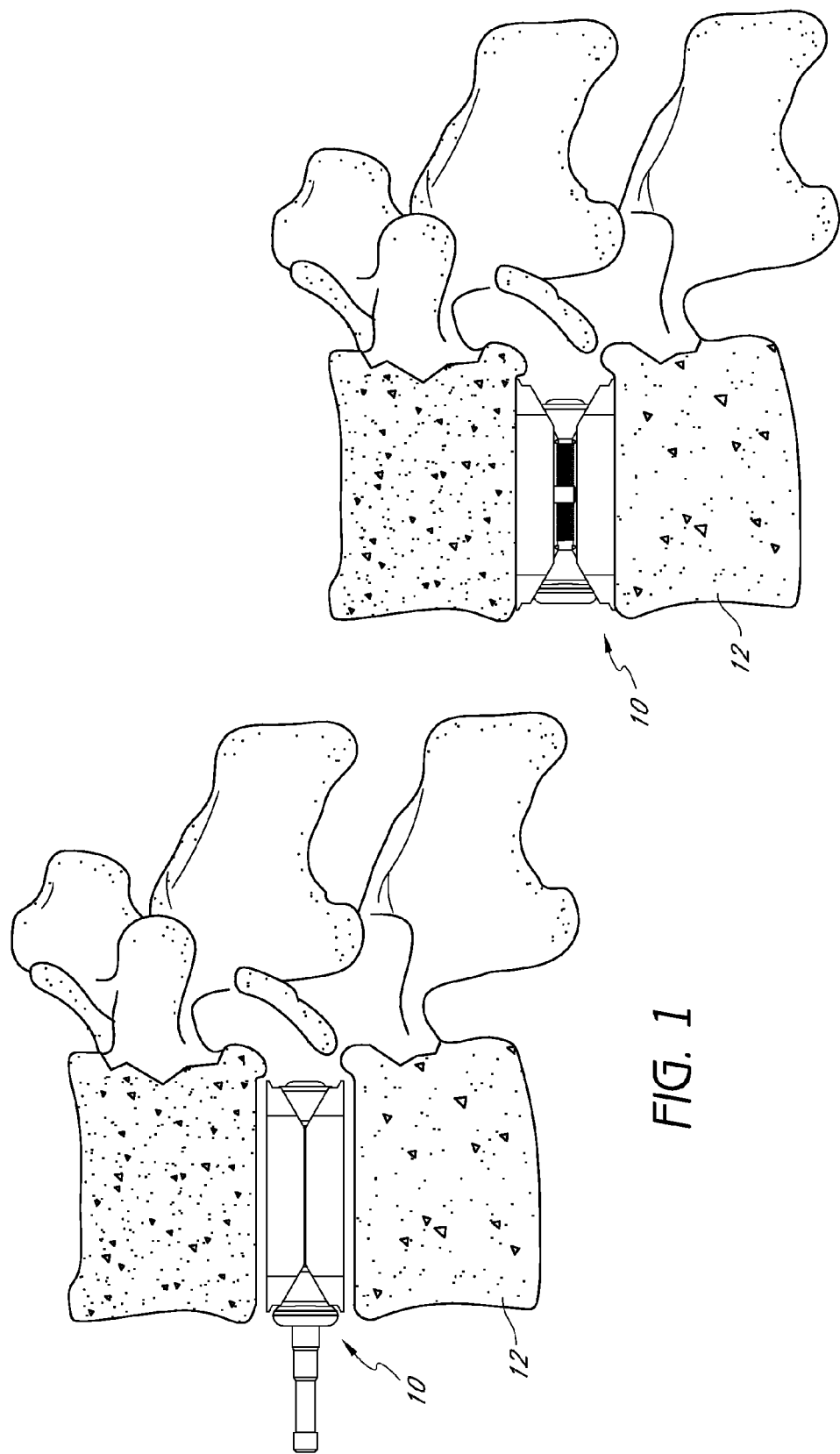

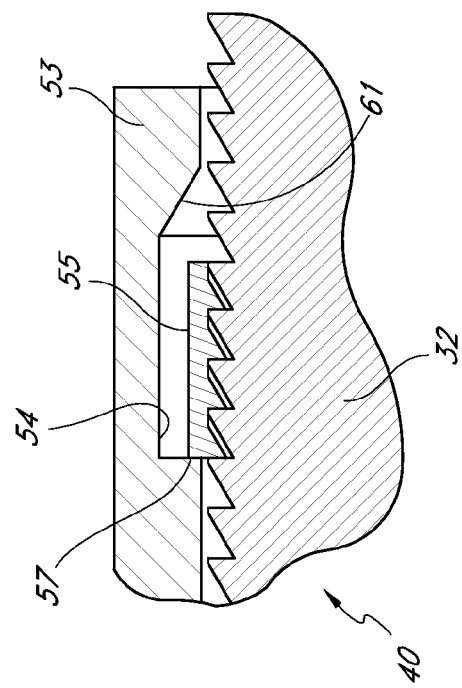
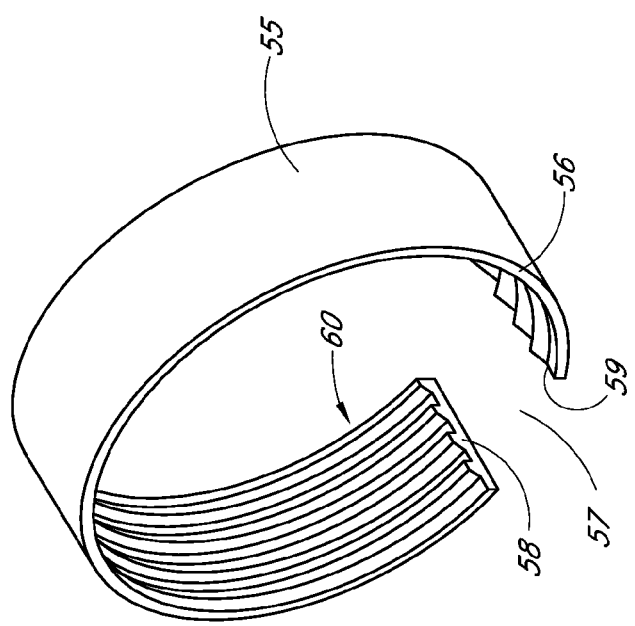
FIG. 9A
FIG. 9B

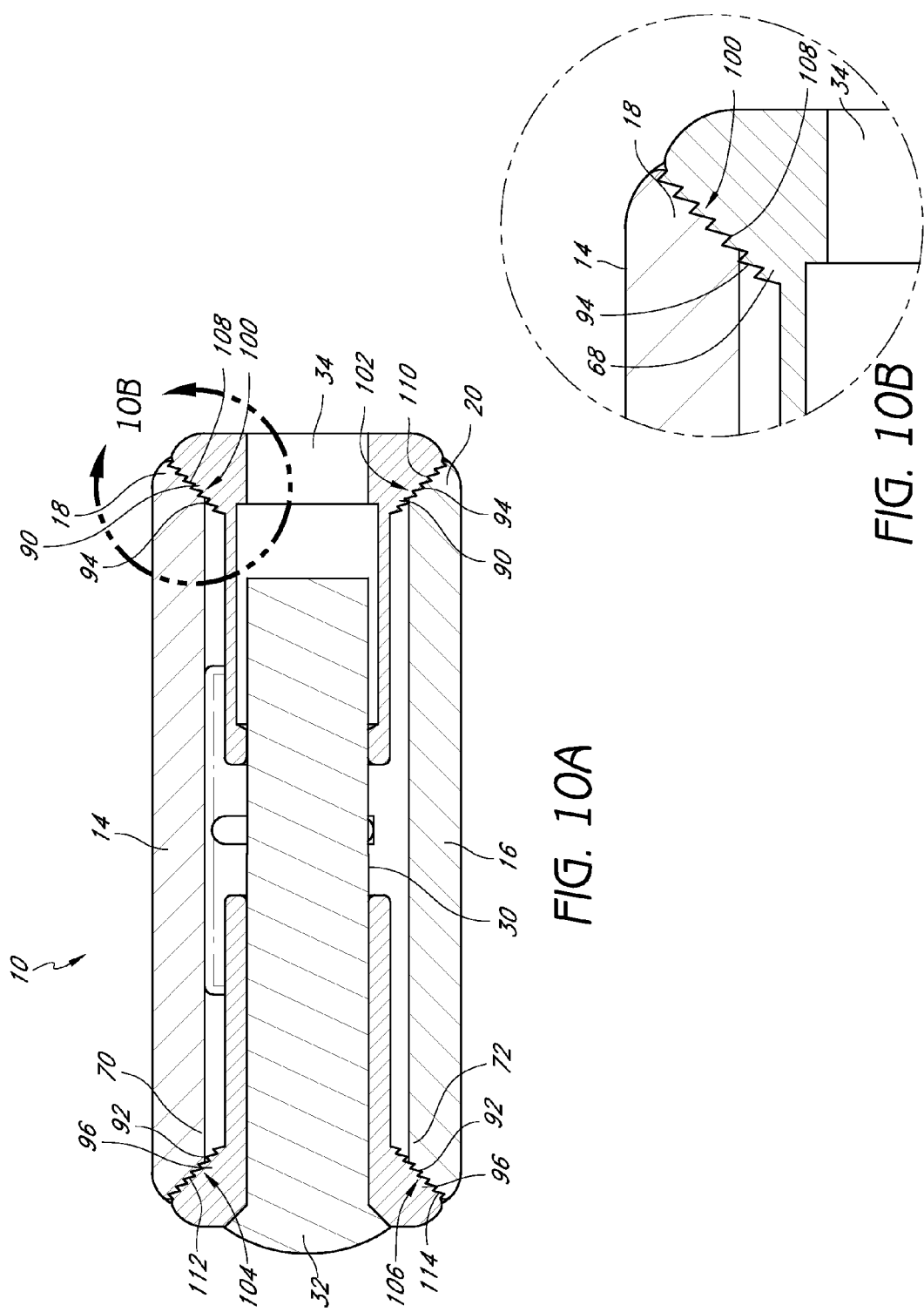

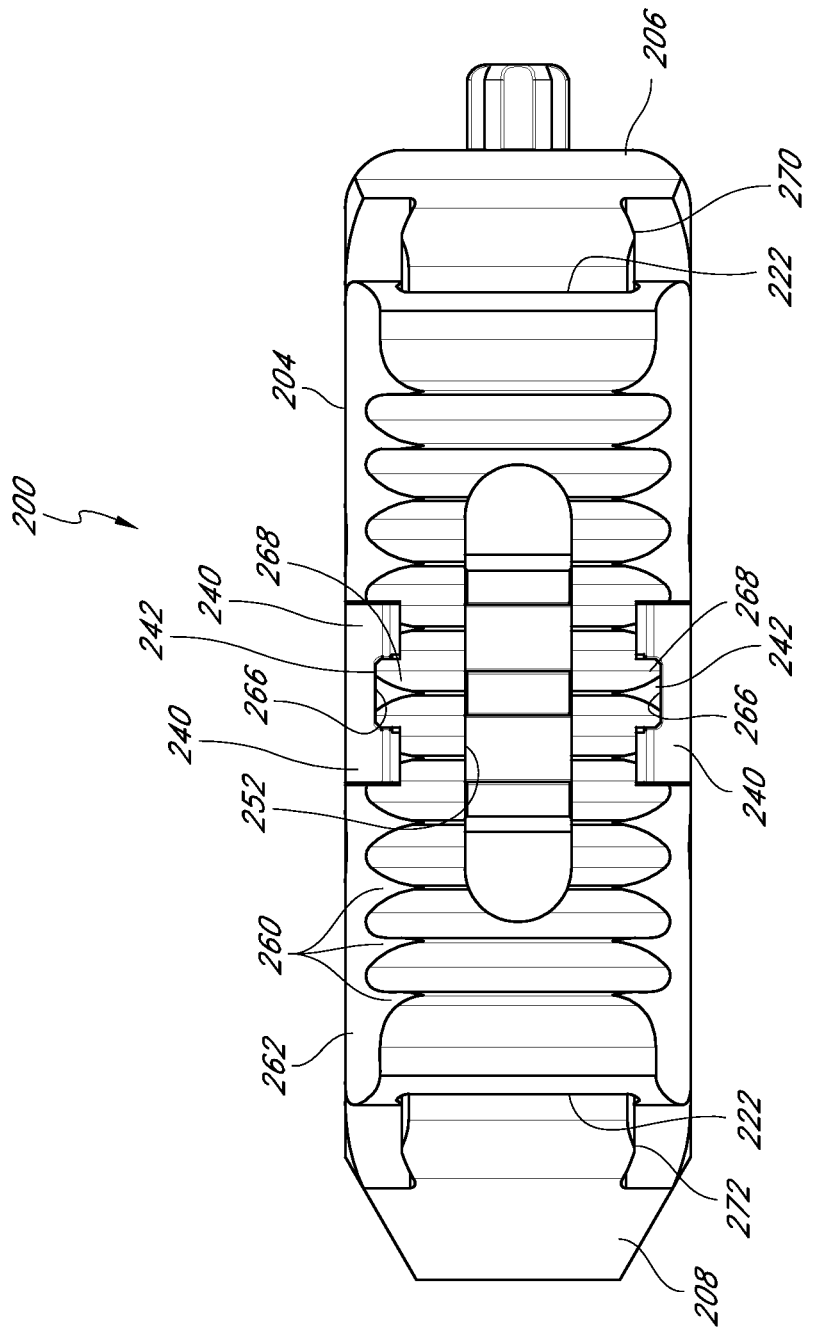

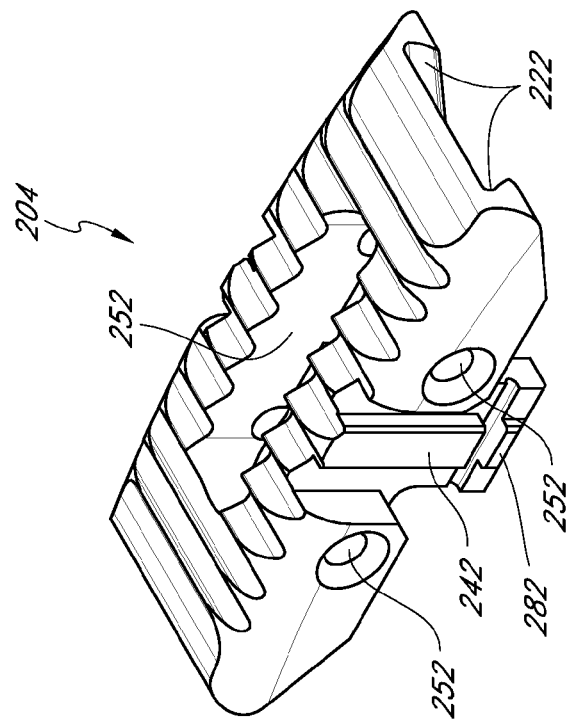
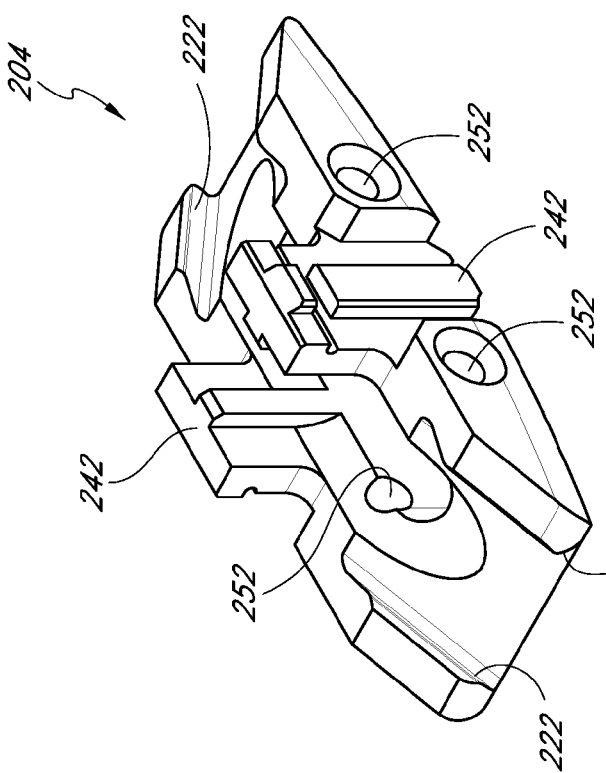
FIG. 20A
FIG. 20B

INTERVERTEBRAL IMPLANT

PRIORITY INFORMATION

The present application is a continuation of U.S. application Ser. No. 11/952,900, filed Dec. 7, 2007, which claims the priority benefit of U.S. Provisional Application Ser. No. 60/869,088, filed Dec. 7, 2006. The entire contents of these applications are hereby incorporated by reference herein.

BACKGROUND

1. Field of the Invention

The present invention relates to medical devices and, more particularly, to an intervertebral implant.

2. Description of the Related Art

The human spine is a flexible weight bearing column formed from a plurality of bones called vertebrae. There are thirty three vertebrae, which can be grouped into one of five regions (cervical, thoracic, lumbar, sacral, and coccygeal). Moving down the spine, there are generally seven cervical vertebra, twelve thoracic vertebra, five lumbar vertebra, five sacral vertebra, and four coccygeal vertebra. The vertebra of the cervical, thoracic, and lumbar regions of the spine are typically separate throughout the life of an individual. In contrast, the vertebra of the sacral and coccygeal regions in an adult are fused to form two bones, the five sacral vertebra which form the sacrum and the four coccygeal vertebra which form the coccyx.

In general, each vertebra contains an anterior, solid segment or body and a posterior segment or arch. The arch is generally formed of two pedicles and two laminae, supporting seven processes—four articular, two transverse, and one spinous. There are exceptions to these general characteristics of a vertebra. For example, the first cervical vertebra (atlas vertebra) has neither a body nor spinous process. In addition, the second cervical vertebra (axis vertebra) has an odontoid process, which is a strong, prominent process, shaped like a tooth, rising perpendicularly from the upper surface of the body of the axis vertebra. Further details regarding the construction of the spine may be found in such common references as Gray's Anatomy, Crown Publishers, Inc., 1977, pp. 33-54, which is herein incorporated by reference.

The human vertebrae and associated connective elements are subjected to a variety of diseases and conditions which cause pain and disability. Among these diseases and conditions are spondylosis, spondylolisthesis, vertebral instability, spinal stenosis and degenerated, herniated, or degenerated and herniated intervertebral discs. Additionally, the vertebrae and associated connective elements are subject to injuries, including fractures and torn ligaments and surgical manipulations, including laminectomies.

The pain and disability related to the diseases and conditions often result from the displacement of all or part of a vertebra from the remainder of the vertebral column. Over the past two decades, a variety of methods have been developed to restore the displaced vertebra to their normal position and to fix them within the vertebral column. Spinal fusion is one such method. In spinal fusion, one or more of the vertebra of the spine are united together ("fused") so that motion no longer occurs between them. Thus, spinal fusion is the process by which the damaged disc is replaced and the spacing between the vertebrae is restored, thereby eliminating the instability and removing the pressure on neurological elements that cause pain.

Spinal fusion can be accomplished by providing an intervertebral implant between adjacent vertebrae to recreate the natural intervertebral spacing between adjacent vertebrae. Once the implant is inserted into the intervertebral space, osteogenic substances, such as autogenous bone graft or bone allograft, can be strategically implanted adjacent the implant to prompt bone ingrowth in the intervertebral space. The bone ingrowth promotes long-term fixation of the adjacent vertebrae. Various posterior fixation devices (e.g., fixation rods, screws etc.) can also be utilize to provide additional stabilization during the fusion process.

Recently, intervertebral implants have been developed that allow the surgeon to adjust the height of the intervertebral implant. This provides an ability to intra-operatively tailor the intervertebral implant height to match the natural spacing between the vertebrae. This reduces the number of sizes that the hospital must keep on hand to match the variable anatomy of the patients.

In many of these adjustable intervertebral implants, the height of the intervertebral implant is adjusted by expanding an actuation mechanism through rotation of a member of the actuation mechanism. In some intervertebral implants, the actuation mechanism is a screw or threaded portion that is rotated in order to cause opposing plates of the implant to move apart. In other implants, the actuation mechanism is a helical body that is counter-rotated to cause the body to increase in diameter and expand thereby.

Furthermore, notwithstanding the variety of efforts in the prior art described above, these intervertebral implants and techniques are associated with another disadvantage. In particular, these techniques typically involve an open surgical procedure, which results higher cost, lengthy in-patient hospital stays and the pain associated with open procedures.

Therefore, there remains a need in the art for an improved intervertebral implant. Preferably, the implant is implantable through a minimally invasive procedure. Further, such devices are preferably easy to implant and deploy in such a narrow space and opening while providing adjustability and responsiveness to the clinician.

SUMMARY OF THE INVENTION

Accordingly, one embodiment of the present invention comprises a spinal fusion intervertebral implant that includes upper and lower body portions and an actuator shaft that can be sized and configured to be received therebetween. The upper and lower body portions can each have proximal surfaces disposed at proximal ends thereof. The actuator shaft can comprise an inner member and an outer sleeve member adapted to be translatable relative to the inner member. The inner member can have distal and proximal ends and at least one retention structure disposed therebetween. The outer sleeve member can have a proximal end and at least one complementary retention structure being sized and configured to engage the retention structure of the inner member to facilitate selective relative movement of the proximal end of the outer sleeve member toward the distal end of the inner member without rotation.

Further, the intervertebral implant can also include at least one proximal wedge member which can be disposed at the proximal end of the outer sleeve member. The proximal protrusion can be sized and configured to contact the proximal surfaces of the upper and lower body portions upon selective relative movement of the proximal end of the outer sleeve member toward the distal end of the inner member. The longitudinal movement of the proximal wedge member against the proximal surfaces can cause the separation of the upper and lower body portions.

In accordance with another embodiment, a spinal fusion intervertebral implant is provided that comprises upper and lower body portions each having proximal and distal surfaces at proximal and distal ends thereof. The proximal and distal surfaces of the upper and lower body portions can be configured to generally face each other. The implant can further comprise an actuator shaft received between the upper and lower body portions. The actuator shaft can comprise an inner member and an outer sleeve member selectively moveable relative to the inner member. The implant can further comprise a distal wedge member disposed at a distal end of the inner member. The distal wedge member can have an engagement surface configured to provide ratchet-type engagement with the distal surfaces of the upper and lower body portions upon selective relative movement of the distal end of the inner member toward the proximal end of the outer sleeve member. Further, the implant can comprise a proximal wedge member disposed at a proximal end of the outer sleeve member. The proximal wedge member can have an engagement surface configured to provide ratchet-type engagement with the proximal surfaces of the upper and lower body portions upon selective relative movement of the proximal end of the outer sleeve member toward the distal end of the inner member. In such an embodiment, longitudinal movement of the distal wedge member against the distal surfaces and the longitudinal movement of the proximal wedge member against the proximal surfaces can cause separation of the upper and lower body portions. Furthermore, the ratchet-type engagement between the distal and proximal wedge members and the respective ones of the proximal and distal surfaces of the upper and lower body portions can maintain separation of the upper and lower body portions.

In accordance with yet another embodiment, a method of implanting a implant is also provided. The method can comprise the steps of positioning the implant between two vertebral bodies and moving an inner member of an actuator shaft of the implant in an proximal direction relative to an outer sleeve member disposed about the inner sleeve member to force a proximal protrusion of the outer sleeve member against proximal surfaces of respective ones of upper and lower body portions of the implant to separate the upper and lower body portions to cause the implant to expand intermediate the vertebral bodies.

In accordance with yet another embodiment, a method of implanting a implant is also provided. The method can comprise the steps of positioning the implant between two vertebral bodies and rotating a screw mechanism of the implant to cause proximal and distal wedge members to converge toward each other and engage respective ones of proximal and distal surfaces of upper and lower body portions of the implant to separate the upper and lower body portions to cause the implant to expand.

In accordance with yet another embodiment, an adjustable spinal fusion intervertebral implant is provided that comprises upper and lower body portions, proximal and distal wedge members, and a pin.

The upper and lower body portions can each have proximal and distal surfaces at proximal and distal ends thereof. The proximal and distal surfaces of the upper and lower body portions can generally face each other. The proximal surfaces of the respective ones of the upper and lower body portions can each define a proximal slot therein. The distal surfaces of the respective ones of the upper and lower body portions can each define a distal slot therein.

The proximal wedge member can be disposed at the proximal ends of the respective ones of the upper and lower body portions. The proximal wedge member can comprise upper and lower guide members extending at least partially into the respective ones of the proximal slots of the upper and lower body portions with at least a portion of the proximal wedge member contacting the proximal surfaces of the upper and lower body portions. The distal wedge member can be disposed at the distal ends of the respective ones of the upper and lower body portions. The distal wedge member can comprise upper and lower guide members extending at least partially into the respective ones of the distal slots of the upper and lower body portions with at least a portion of the distal wedge member contacting the distal surfaces of the upper and lower body portions.

The actuator shaft can be received between the upper and lower body portions. The actuator shaft can extend intermediate the distal and proximal wedge members, wherein rotation of the actuator shaft causes the distal and proximal wedge members to be drawn together such that longitudinal movement of the distal wedge member against the distal surfaces and the longitudinal movement of the proximal wedge member against the proximal surfaces causes separation of the upper and lower body portions.

In such an embodiment, the upper body portion can further comprise a pair of downwardly extending side members and the lower body portion further comprises a pair of upwardly extending side members. The side members of the upper body portion can engage the side members of the lower body portion to facilitate linear translational movement of the upper body portion relative to the lower body portion. The side members of the upper body portion can each comprise a slot and the side members of the lower body portion each comprise a guide member. The guide members of the side members of the lower body portion can each be received into the slots of the side members of the upper body portion.

The implant can be configured wherein the proximal and distal surfaces of the upper and lower body portions are sloped. The slots of the proximal and distal surfaces of the upper and lower body portions can also be sloped. Further, the slots of the proximal and distal surfaces of the upper and lower body portions can be generally parallel to the respective proximal and distal surfaces of the upper and lower body portions. In other embodiments, the slots of the proximal and distal surfaces of the upper and lower body portions can be generally dove-tailed. The guide members of the proximal and distal wedge members can also be generally dovetailed. In other embodiments, the upper and lower body portions can comprise generally arcuate respective upper and lower exterior engagement surfaces.

The proximal wedge member can comprise an anti-rotational element. The anti-rotational engagement can be configured to be engaged by an implant tool for preventing rotation of the implant when the actuator shaft is rotated relative to the implant. The anti-rotational element can comprise a pair of apertures extending into the proximal wedge member.

In yet another embodiment, an implantation tool is provided for implanting an expandable intervertebral implant. The tool can comprise a handle section, a distal engagement section, and an anti-rotational engagement member. The handle section can comprise a fixed section and first and second rotatable members. The distal engagement section can comprise a fixed portion and first and second rotatable portions being operatively coupled to the respective ones of the first and second rotatable members. The first rotatable portion can comprise a distal attachment element. The distal engagement element can be operative to be removably attached to a distal end of at least a portion of the implant. The second rotatable portion can comprise a distal engagement member being configured to engage a proximal end of an actuator shaft of the implant for rotating the actuator shaft to thereby and expanding the implant from an unexpanded state to and expanded state. The anti-rotational engagement member can be used to engage an anti-rotational element of the implant.

In some embodiments, the first and second rotatable members of the tool can be coaxially aligned. Further, the first and second rotatable portions can be coaxially aligned. The first and second rotatable portions can be tubular, and the first rotatable portion can be disposed internally to the second rotatable portion. The fixed portion of the distal engagement section can be tubular and the first and second rotatable portions can be disposed internally to the fixed portion.

BRIEF DESCRIPTION OF THE DRAWINGS

FIG. 1 is a side view of an intervertebral implant in an unexpanded state while positioned intermediate adjacent vertebrae, according to an embodiment.

FIG. 2 is a side view of the intervertebral implant shown in FIG. 1 in an expanded state.

FIG. 9A is a side perspective view of a portion of a modified embodiment of the outer sleeve member.

FIG. 9B is an enlarged longitudinal cross-sectional view of a modified embodiment of the outer sleeve member with the portion shown in FIG. 9A.

FIG. 10A is a side cross sectional view of another embodiment of an intervertebral implant.

FIG. 10B is an enlarged view of the section 10B shown in FIG. 10A.

FIG. 17 is a bottom view of the intervertebral implant shown in FIG. 16A.

FIG. 20A is a bottom perspective view of a lower body portion of the intervertebral implant shown in FIG. 16A.

FIG. 20B is a top perspective view of the lower body portion of the intervertebral implant shown in FIG. 16A.

DETAILED DESCRIPTION OF THE PREFERRED EMBODIMENTS

Figure 3:
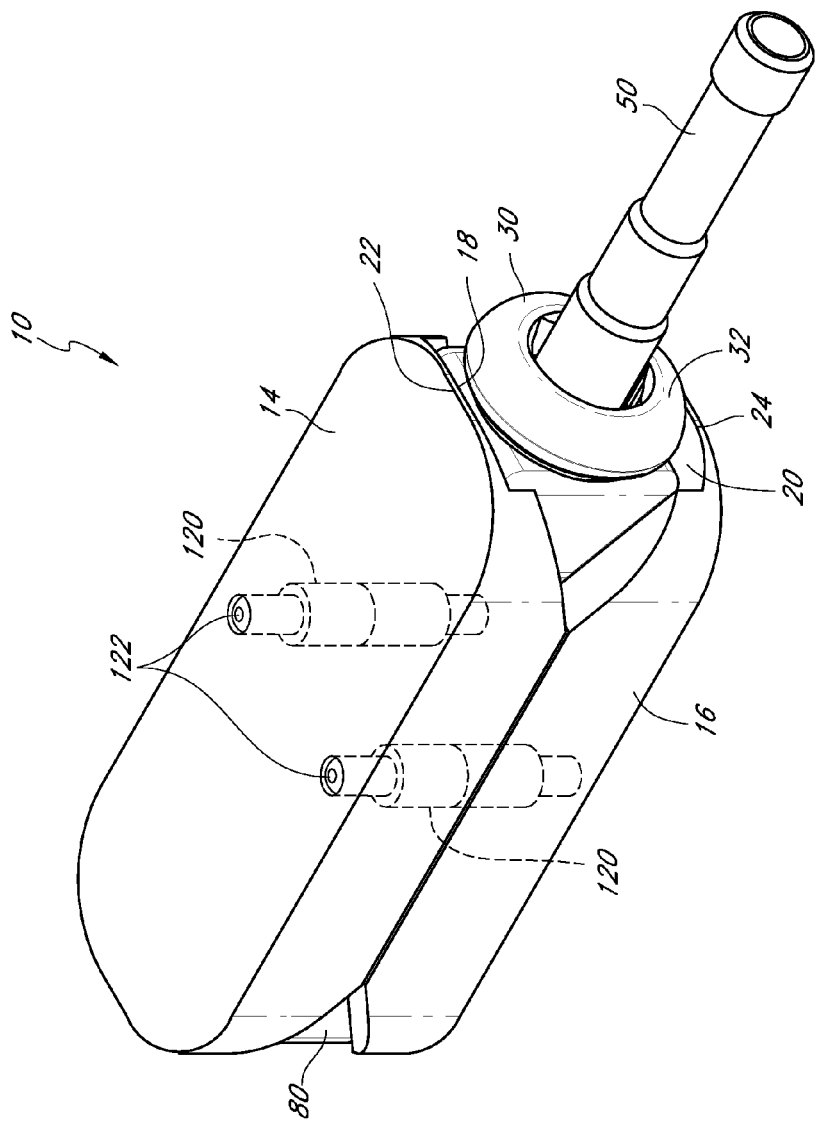
FIG. 3 is a perspective view of the intervertebral implant shown in FIG. 1 in an unexpanded state.

In accordance with certain embodiments disclosed herein, an improved intervertebral implant is provided that allows the clinician to insert the intervertebral implant through a minimally invasive procedure. For example, in one embodiment, one or more intervertebral implants can be inserted percutaneously to reduce trauma to the patient and thereby enhance recovery and improve overall results of the surgery.

For example, in one embodiment, an intervertebral implant includes a plurality of body sections that are selectively separable and expandable upon contraction of a centrally disposed actuator. The actuator can be utilized to contract against faces of the body sections to cause the expansion thereof. The implant can also be configured such that the actuator provides for both the expansion and contraction of the body sections. The actuator can comprise an interaction between the body sections and another element, an action performed by another element, or a combination of interactions between various elements of the implant and its body sections. Further, the implant can be configured to allow either rough or fine incremental adjustments in the expansion of the implant.

The embodiments disclosed herein are discussed in the context of an intervertebral implant and spinal fusion because of the applicability and usefulness in such a field. As such, various embodiments can be used to properly space adjacent vertebrae in situations where a disc has ruptured or otherwise been damaged. As also disclosed herein, embodiments can also be used as vertebral body replacements. Thus, "adjacent" vertebrae can include those originally separated only by a disc or those that are separated by intermediate vertebra and discs. Such embodiments can therefore tend to recreate proper disc height and spinal curvature as required in order to restore normal anatomical locations and distances. However, it is contemplated that the teachings and embodiments disclosed herein can be beneficially implemented in a variety of other operational settings, for spinal surgery and otherwise.

For example, the implant disclosed herein can also be used as a vertebral body replacement. In such a use, the implant could be used as a replacement for a lumbar vertebra, such as one of the L1-L5 vertebrae. Thus, the implant could be appropriately sized and configured to be used intermediate adjacent vertebrae, or to entirely replace a damaged vertebra.

It is contemplated that the implant can be used as an interbody or intervertebral device or can be used to replace a vertebral body entirely. The implant can also be used in veterbal body compression fractures. Further, the implant can be used as a tool to expand an intervertebral space or bone in order to fill the space or bone with a cement; in such cases, the implant can be removed or left in once the cement is placed. Furthermore, the implant can also be used as a tool to predilate disc space. In some embodiments, the implant can be removed once the disc space is dilated, and a different implant (expandable or non-expandable) can then be implanted in the dilated disc space. Finally, the implant can also be introduced into the disc space anteriorly in an anterior lumbar interbody fusion (ALIF) procedure, posterior in an posterior lumbar interbody fusion (PILF) or posterial lateral interbody fusion, from extreme lateral position in an extreme lateral interbody fusion procedure, and transforaminal lumbar interbody fusion (TLIF), to name a few. Although the implant is primarily described herein as being used to expand in a vertical direction, it can also be implanted to expand in a horizontal direction in order to increase stability and/or increase surface area between adjacent vertebral bodies.

Additionally, the implant can comprise one or more height change mechanisms to facilitate expansion of the implant. For example, the implant can use a classic wedge system, a parallel bar and linkage system, a jack system, a pair of inclined planes, a screw jack system, a cam system, a balloon and bellows system, a hydraulic or pneumatic system, a longitudinal deformation/crush system (in which longitudinal contraction creates vertical expansion), or a stacking system, to name a few. Furthermore, the implant can comprise one or more height retention mechanisms. For example, the implant can use a pin ratchet system, a wedge ratchet system, a lead screw system with left or right-hand threads, or a lead screw system with left and right-hand threads, to name a few.

Therefore, it is contemplated that a number of advantages can be realized utilizing various embodiments disclosed herein. For example, as will be apparent from the disclosure, no external distraction of the spine is necessary. Further, no distraction device is required in order to install various embodiments disclosed herein. In this regard, embodiments of the implant can enable sufficient distraction of adjacent vertebra in order to properly restore disc height or to use the implant as a vertebral body replacement. Thus, normal anatomical locations, positions, and distances can be restored and preserved utilizing many of the embodiments disclosed herein.

Referring to FIG. 1, there is illustrated a side view of an embodiment of a intervertebral implant 10 in an unexpanded state while positioned generally between adjacent vertebrae of the lumbar portion of the spine 12. FIG. 2 illustrates the intervertebral implant 10 in an expanded state, thereby supporting the vertebrae in a desired orientation and spacing in preparation for spinal fusion. As is known in the art, spinal fusion is the process by which the adjacent vertebrae of the spine are united together ("fused") so that motion no longer occurs between the vertebrae. Thus, the intervertebral implant 10 can be used to provide the proper spacing two vertebrae to each other pending the healing of a fusion. See also U.S. Patent Publication No. 2004/0127906, filed Jul. 18, 2003, application Ser. No. 10/623,193, the entirety of the disclosure of which is hereby incorporated by reference.

According to an embodiment, the implant can be installed in an operation that generally entails the following procedures. The damaged disc or vertebra can be decompressed, such as by distracting. The subject portion (or entire) disc or vertebra can then be removed. The adjacent vertebrae can be prepared by scraping the exposed adjacent portion or plates thereof (typically to facilitate bleeding and circulation in the area). Typically, most of the nucleus of the disc is removed and the annulus of the disc is thinned out. Although individual circumstances may vary, it may be unusual to remove all of the annulus or to perform a complete diskectomy. The implant can then be installed. In some embodiments, distraction of the disc may not be a separate step from placement of the implant; thus, distraction can be accomplished and can occur during placement of the implant. Finally, after implantation of the implant, osteogenic substances, such as autogenous bone graft, bone allograft, autograft foam, or bone morphogenic protein (BMP) can be strategically implanted adjacent the implant to prompt bone ingrowth in the intervertebral space. In this regard, as the implant is expanded, the spaces within the implant can be backfilled; otherwise, the implant can be prepacked with biologics.

The intervertebral implant is often used in combination with posterior and/or anterior fixation devices (e.g., rods, plates, screws, etc. that span two or more vertebrae) to limit movement during the fusion process. U.S. Patent Publication No. 2004/0127906 discloses a particularly advantageous posterior fixation device and method which secures two adjacent vertebra to each other in a trans-laminar, trans-facet or facet-pedicle (e.g., the Boucher technique) application using fixation screws.

It should also be appreciated that in FIGS. 1 and 2 only one intervertebral implant 10 is shown positioned between the vertebrae 12. However, as will be discussed in more detail below, it is anticipated that two, three or more implants 10 can be inserted into the space between the vertebrae. Further, other devices, such as bone screws, can be used on the vertebrae as desired. For example, in a spinal fusion procedure, it is contemplated that one or more implants 10 can be used in conjunction with one or more bone screws and/or dynamic stabilization devices, such as those disclosed in the above-mentioned U.S. Patent Publication No. 2004/0127906, filed Jul. 18, 2003, application Ser. No. 10/623,193.

In another embodiment of use, the implant 10 can be used in combination with a dynamic stabilization devices such as those disclosed in U.S. Patent Publication No. 2006-0122609, filed Feb. 11, 2005, application Ser. No. 11/056,991; U.S. Patent Publication No. 2005/0033289, filed on May 6, 2004, now U.S. Pat. No. 6,951,561; U.S. Provisional Patent Application No. 60/942,998, filed on Jun. 8, 2007; U.S. Provisional Application No. 60/397,588 filed Jul. 19, 2002; U.S. Provisional Application No. 60/424,055, filed Nov. 5, 2002; Ser. No. 10/623,193; U.S. Provisional Application No. 60/397,588 filed Jul. 19, 2002 and Provisional Application 60/424,055 filed Nov. 5, 2002; the entireties of the disclosures of which are hereby incorporated by reference. In this manner, the implant 10 can be used to maintain height between vertebral bodies while the dynamic stabilization device provides limits in one or more degrees of movement.

Figure 4:
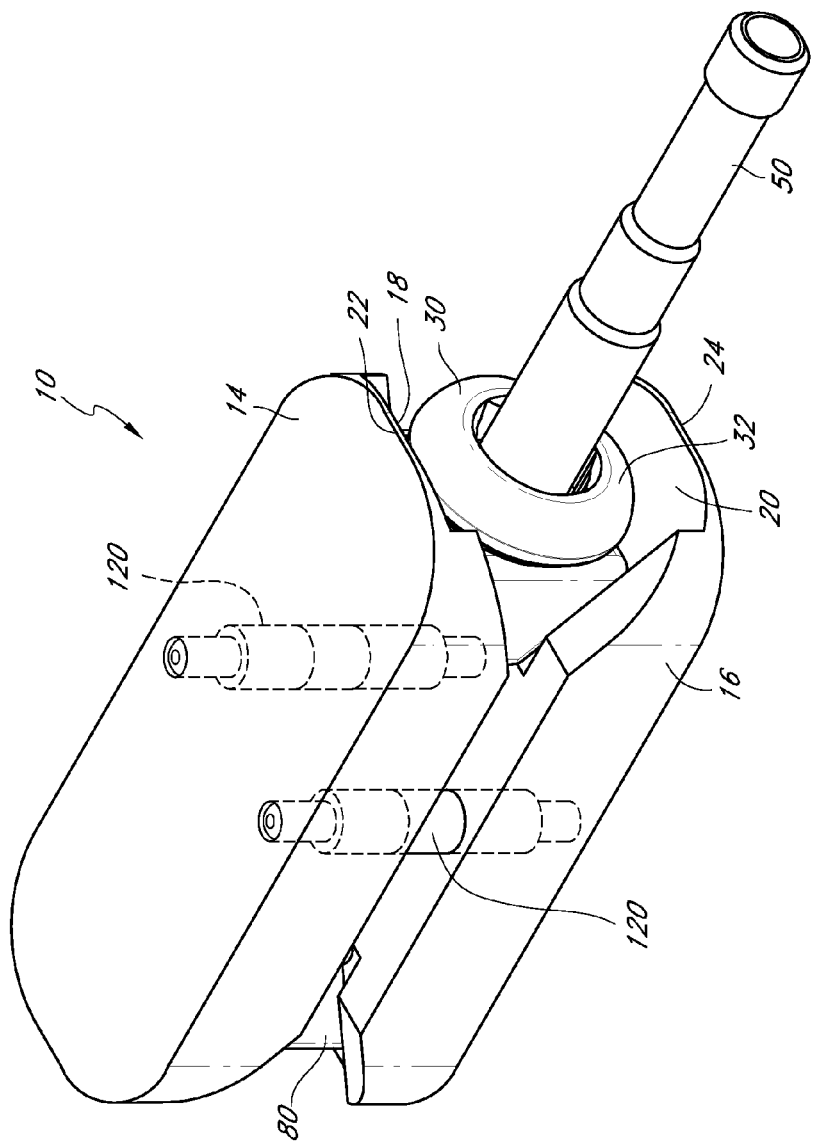
FIG. 4 is a perspective view of the intervertebral implant shown in FIG. 3 in an expanded state.

The embodiment of the intervertebral implant 10 shown FIGS. 1 and 2 will now be described in more detail with reference FIGS. 3 and 4. FIG. 3 illustrates a perspective view the intervertebral implant 10 in an unexpanded state while FIG. 4 illustrates the intervertebral implant 10 in an expanded state. The intervertebral implant 10 can comprise an upper body portion 14 and a lower body portion 16. The upper and lower body portions 14, 16 can each have a proximally facing surface 18, 20 disposed at respective proximal ends 22, 24 thereof and generally facing each other. As will be explained below, the proximally facing surfaces 18, 20 can be inclined or otherwise curved with respect to the longitudinal axis of the body portions 14, 16.

In the illustrated embodiment, the upper and lower body portions 14, 16 are illustrated as being configured substantially as parallel plate like structures. As will be explained below, the upper and lower body portions 14, 16 can be variously configured and designed, such as being generally ovular, wedge-shaped, and other shapes. For example, instead of including smooth exterior surfaces, as shown, the upper and lower body portions 14, 16 can be configured to include a surface texture, such as one or more external teeth, in order to ensure that the intervertebral implant 10 is maintained in a given lateral position once expanded intermediate the adjacent vertebrae of the spine 12. Other such modifications can be implemented in embodiments disclosed herein, and may be readily understood by one of skill in the art.

The intervertebral implant 10 can further comprise an actuator shaft 30 that can be sized and configured to be received between the upper and lower body portions 14, 16. As described herein with respect to various embodiments, the actuator shaft 30 can be utilized not only to move the intervertebral implant 10 from the unexpanded to the expanded state, but also to maintain expansion of the intervertebral implant 10. The actuator shaft 30 can be utilized in several embodiments to provide numerous advantages, such as facilitating precise placement, access, and rapid deployment of the intervertebral implant 10.

Figure 5:
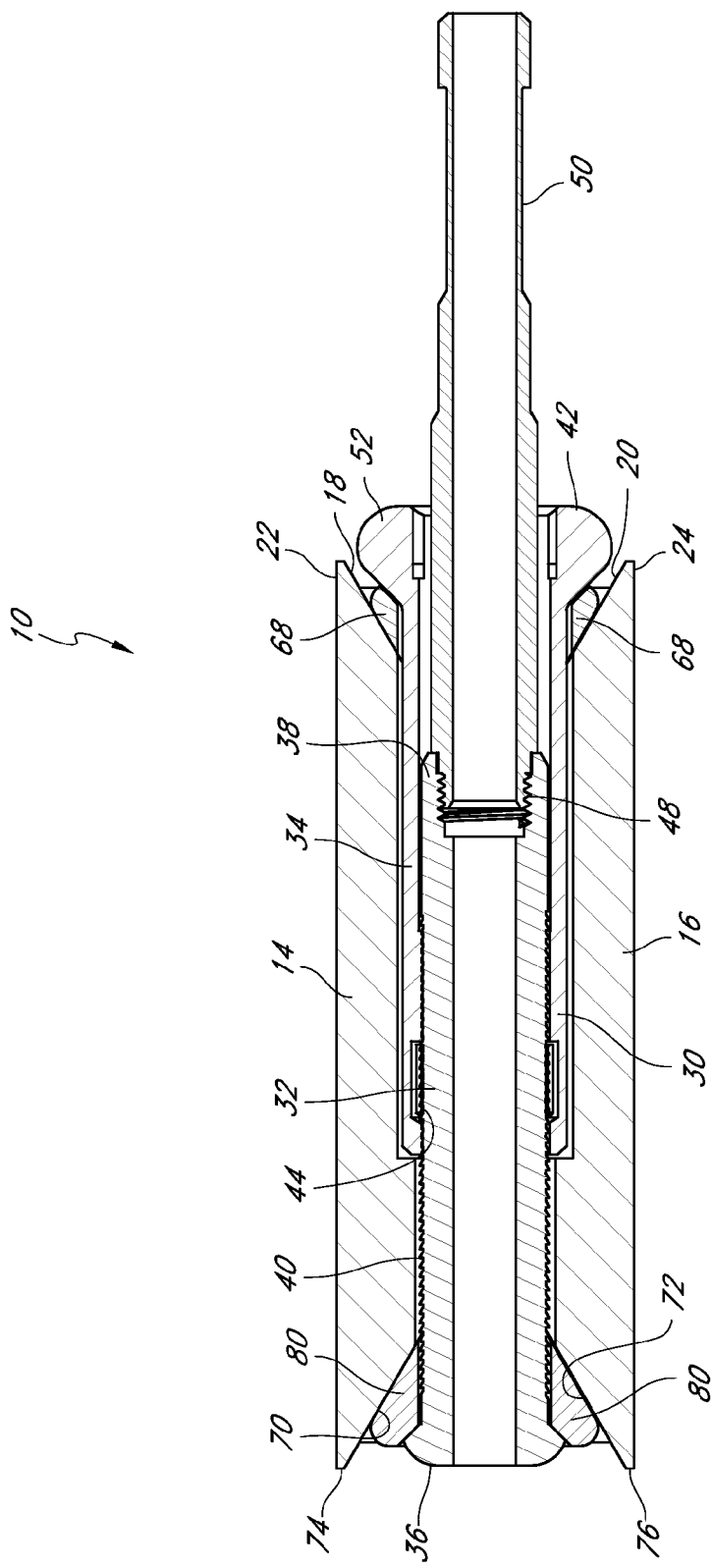
FIG. 5 is a side cross sectional view of the intervertebral implant shown in FIG. 3 in an unexpanded state.
Figure 6:
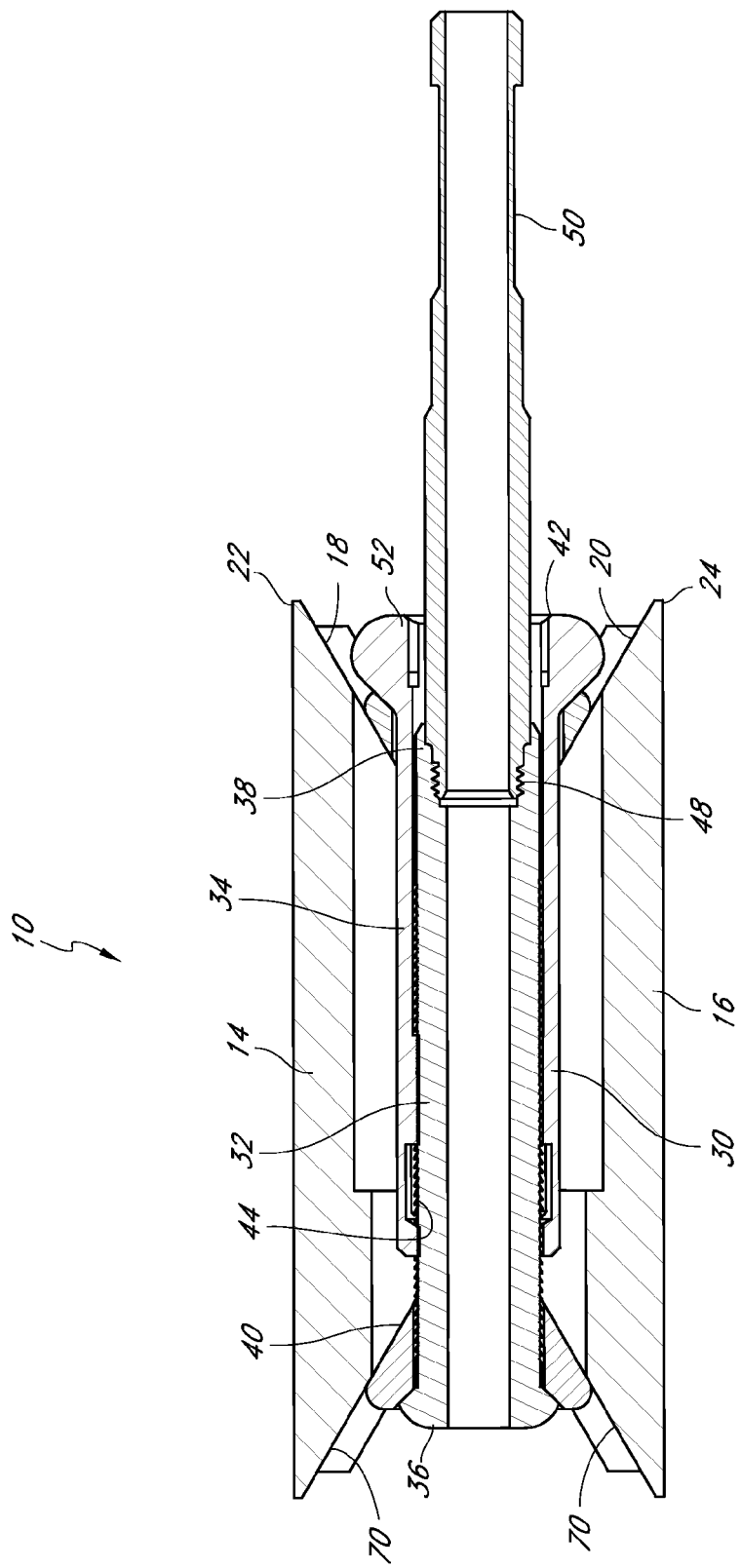
FIG. 6 is a side cross-sectional view of the intervertebral implant shown in FIG. 5 in an expanded state.

As shown in FIGS. 5 and 6, the actuator shaft 30 can comprise an inner member 32 and an outer sleeve member 34. In accordance with an embodiment, the outer sleeve member 34 can be adapted to be translatable relative to the inner member 32 such that the distance between the distal end of the inner member 32 and the proximal end of the outer member 34 can be reduced or shortened. The inner member 32 can have a distal end 36, a proximal end 38, and at least one retention structure 40 disposed therebetween. The outer sleeve member 32 can also have a proximal end 42 and at least one complementary retention structure 44.

In general, the retention structures 40, 44 between the inner member 32 and the outer member 34 can be configured such that facilitate selective relative movement of the proximal end 42 of the outer sleeve member 34 with respect to the distal end 36 of the inner member 32. While permitting such selective relative movement, the structures 40, 44 are preferably configured to resist movement once the distance between the proximal end 42 of the outer sleeve member 34 with respect to the distal end 36 of the inner member 32 is set. As will be described below, the retention structures 40, 44 can comprise any of a variety threads or screw-like structures, ridges, ramps, and/or ratchet type mechanisms which those of skill in the art will recognize provide such movement.

In some embodiments, the movement of proximal end 42 of the outer sleeve member 34, which may be in a direction distal to the clinician, can be accomplished without rotation of the actuator shaft 30, or any portion thereof. Thus, some embodiments provide that the actuator shaft 30 can be advantageously moved to the engaged position using only substantially longitudinal movement along an axis of the actuator shaft 30. It is contemplated that this axial translation of the outer sleeve member 34 can aid the clinician and eliminate cumbersome movements such as rotation, clamping, or otherwise. In this regard, the clinician can insert, place, and deploy the intervertebral implant 10 percutaneously, reducing the size of any incision in the patient, and thereby improving recovery time, scarring, and the like. These, and other benefits are disclosed herein.

In accordance with another embodiment, the proximal end 38 of the actuator shaft 30 can also be provided with a structure 48 for permitting releasable engagement with an installation or a removal tool 50. The actuator shaft 30 can therefore be moved as required and the tool 50 can later be removed in order to eliminate any substantial protrusions from the intervertebral implant 10. This feature can allow the intervertebral implant 10 to have a discreet profile once implanted into the patient and thereby facilitate healing and bone growth, while providing the clinician with optimal control and use of the intervertebral implant 10.

For example, as shown in FIG. 5, structure 48 comprises interacting threads between the distal end of the tool 50 and the proximal end 38 of the inner member 32. In a modified embodiment, the structure 48 can comprise any of a variety of fixation devices (e.g., hooks, latches, threads, etc.) as will be apparent to those of skill in the art. The actuator shaft 30 can therefore be securely coupled to the tool 50 during implantation of the intervertebral implant 10. Once disposed in the intervertebral space, the clinician can grasp the tool 50 to maintain the inner member 32 of the actuator shaft 30 at a constant position while pushing the outer sleeve member 34 in the distal direction and/or pull on the tool to proximally retract the inner member 32 while maintaining the outer member 34 stationary. Thus, the clinician can effectuate movement of the actuator shaft 30 and/or apply a force the actuator shaft 30. As will be described further below, this movement can thereby cause the intervertebral implant 10 to move from the unexpanded to the expanded state.

Alternatively, the tool 50 can be omitted and/or combined with the actuator shaft 30 such that the actuator shaft 30 includes a proximal portion that extends proximally in order to allow the clinician to manipulate the actuator shaft 30 position, as described with respect to the tool 50. In such an embodiment, the actuator shaft 30 can be provided with a first break point to facilitate breaking a proximal portion of the actuator shaft 30 which projects proximally of the proximal end 42 of the outer sleeve member 34 following tensioning of the actuator shaft 30 and expansion of the intervertebral implant 10. The break point can comprise an annular recess or groove, which can provide a designed failure point if lateral force is applied to the proximal portion while the remainder of the attachment system is relatively securely fixed in the intervertebral space. At least a second break point can also be provided, depending upon the axial range of travel of the outer sleeve member 34 with respect to the inner member 32. Other features and embodiments can be implemented as described in U.S. Pat. No. 6,951,561, the disclosure of which is hereby incorporated by reference in its entirety.

The retention structures 40, 44 of the inner member 32 and the outer sleeve member 34 can thus permit proximal movement of the inner member 32 with respect to the outer sleeve member 34 but resist distal movement of the inner member 32 with respect to the outer sleeve member 34. As the outer sleeve member 34 moves in the distal direction, the complementary retention structures 44 can engage the retention structures 40 of the inner member 32 to allow advancement of the outer sleeve member 34 in a distal direction with respect to inner member 32, but which resist proximal motion of outer sleeve member with respect to inner member 32. This can result in one-way or ratchet-type movement. Thus, in such an embodiment, at least one of the complementary retention structures 44 and the retention structures can comprise a plurality of annular rings, ramps, or ratchet-type structures. As mentioned above, any of a variety of ratchet-type structures can be utilized.

The actuator shaft 30 can also be configured to include a noncircular cross section or to have a rotational link such as an axially-extending spline on the inner member 32 for cooperating with a complementary keyway on the outer sleeve member 34. In another embodiment, the retention structures 40, 44 can be provided on less than the entire circumference of the inner member 32 or outer sleeve member 34, as will be appreciated by those of skill in the art. Thus, ratchet structures can be aligned in an axial strip such as at the bottom of an axially extending channel in the surface of the inner member 32. In this manner, the outer sleeve member 34 can be rotated to a first position to bypass the retention structures 40, 44 during axial advancement and then rotated to a second position to engage the retention structures 40, 44.

In accordance with another embodiment, the retention structures 40 of the inner member 32 can comprise a plurality of threads, adapted to cooperate with the complimentary retention structures 44 on the outer sleeve member 34, which may be a complimentary plurality of threads. In such an embodiment, the outer sleeve member 34 can be distally advanced along the inner member 32 by rotation of the outer sleeve member 34 with respect to the inner member 32, thus causing expansion of the intervertebral implant 10. The outer sleeve member 34 can also advantageously be removed from the inner member 32 by reverse rotation, such as to permit contraction of the intervertebral implant 10 to the unexpanded state in order to adjust the position thereof within the intervertebral space or to facilitate the removal of the intervertebral implant 10 from the patient.

Figure 7:
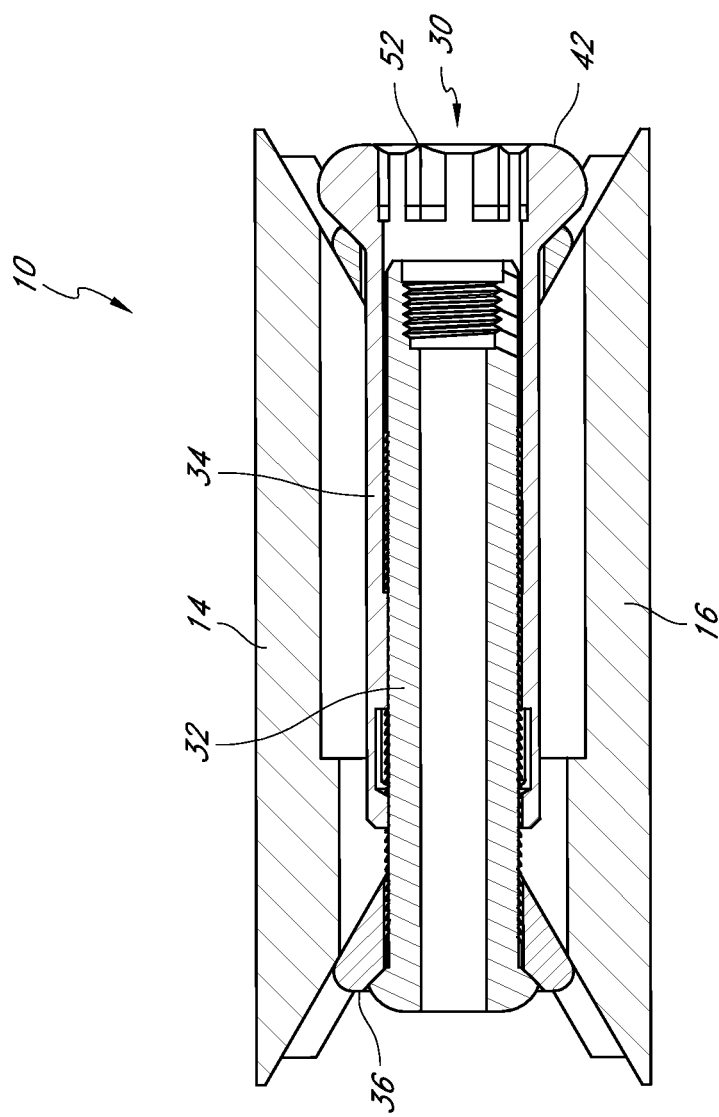
FIG. 7 is a side cross-sectional view of the intervertebral implant shown in FIG. 5 in an expanded state and wherein a portion of an actuator shaft has been removed.
Figure 8:
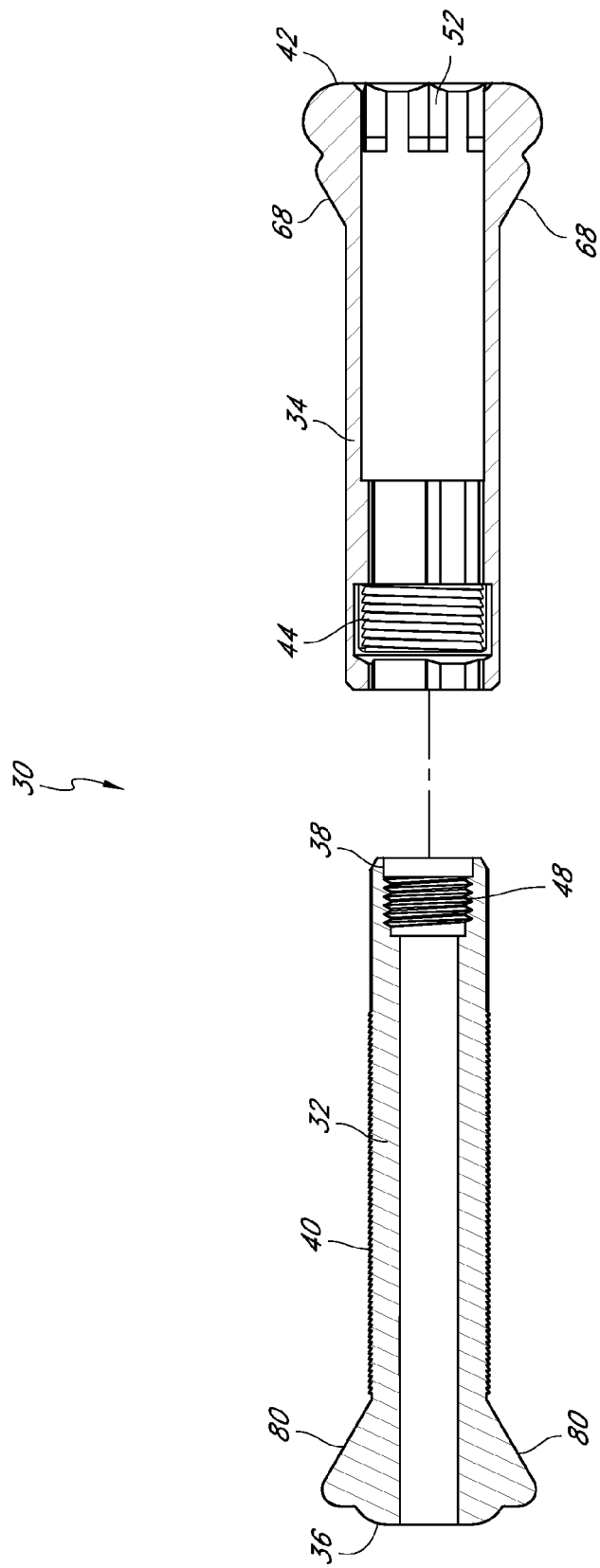
FIG. 8 is a side cross sectional view of another embodiment of the actuator shaft of the intervertebral implant shown in FIG. 3, wherein the actuator shaft has an outer sleeve member and an inner sleeve member.

For such a purpose, the outer sleeve member 34 can be preferably provided with a gripping configuration, structure, or collar 52 (see e.g., FIG. 7) to permit a removal instrument to rotate the outer sleeve member 34 with respect to the inner member 32. For example, such an instrument can be concentrically placed about the tool 50 and engage the collar 52. Thus, while holding the tool 50 in a fixed position, the clinician can reverse rotate the instrument to move the outer sleeve member 34 in a proximal direction. Any of a variety of gripping configurations may be provided, such as one or more slots, flats, bores, or the like. In the illustrated embodiment, the collar 52 can be provided with a polygonal, and in particular, a hexagonal circumference, as seen in FIGS. 7 and 8.

Various embodiments and/or additional or alternative components of the actuator shaft 30 and the retention structures 40, 44 can be found in U.S. Patent Publication 2004/0127906 (U.S. patent application Ser. No. 10/623,193, filed Jul. 18, 2003) entitled "METHOD AND APPARATUS FOR SPINAL FUSION", which is hereby incorporated by reference.

Additional embodiments and/or alternative components of the actuator shaft 30 can be found in U.S. Patent Application No. 60/794,171, filed on Apr. 21, 2006, U.S. Pat. Nos. 6,951, 561, 6,942,668, 6,908,465, and 6,890,333, which are also incorporated by reference. For example, as described in U.S. Pat. No. 6,951,561, the actuator shaft 30 can be configured with particular spacing between the retention structures 40, 44; the actuator shaft 30 dimensions, such as diameter and cross-section, can be variously configured; and the actuator shaft 30 can be manufactured of various types of materials.

Figure 9C:
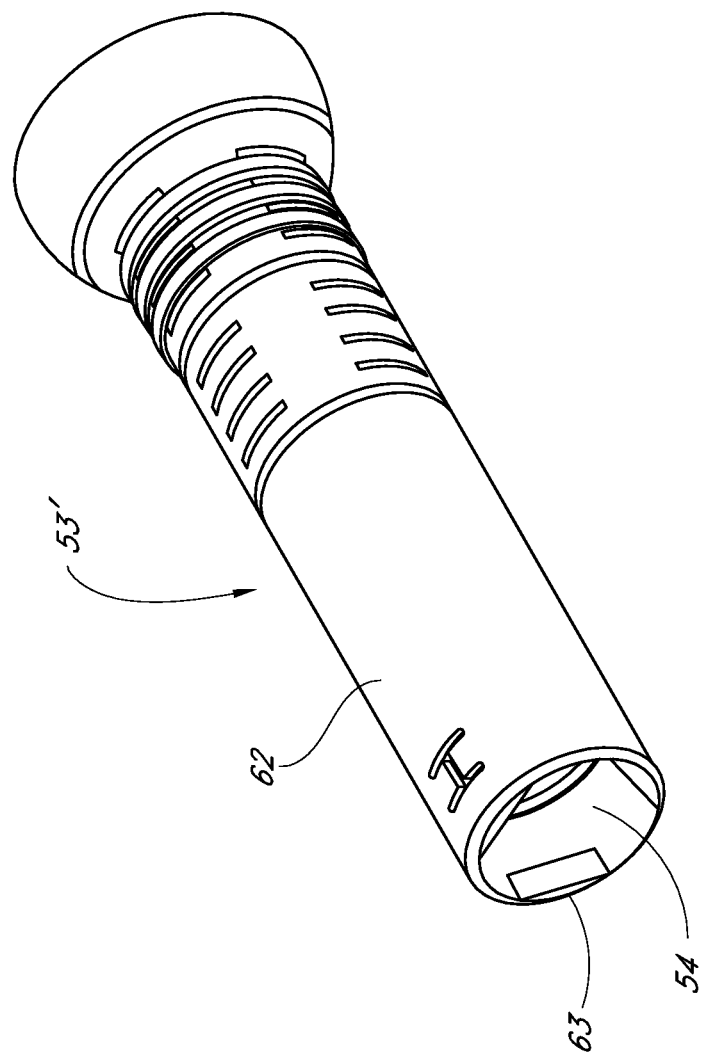
FIG. 9C is a perspective view of another embodiment of an outer sleeve member.
Figure 9E:
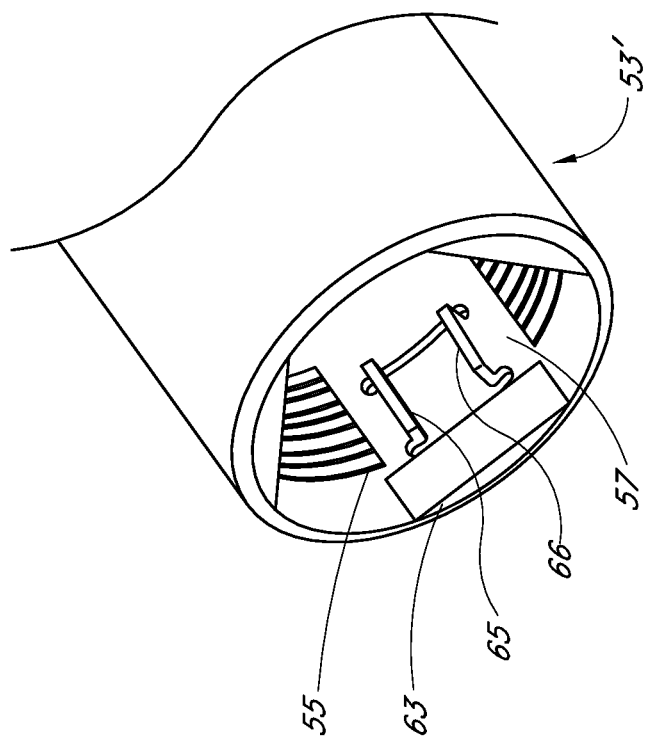
FIGS. 9D and 9E are enlarged views of a portion of one embodiment of an outer sleeve member.

FIGS. 9A and 9B illustrate a portion of a modified embodiment of an outer sleeve member and inner member that is similar to the embodiments described above. In this embodiment, the outer sleeve member preferably includes a recess 54 configured to receive an annular ring 55. In an embodiment, the annular ring 55 can be a split ring (i.e., having a least one gap) and can be interposed between the inner member 32 and the proximal recess 54 of the outer sleeve member. In another embodiment, the ring 55 can be formed from an elastic material configured to ratchet over and engage with the inner member 32. In the split ring embodiment, the ring 55 comprises a tubular housing 56 that may be configured to engage with the inner member 32 and defines a gap or space 57. In one embodiment, the gap 57 is defined by a pair of edges 58, 59. The edges 58, 59 can be generally straight and parallel to each other. However, the edges 58, 59 can have any other suitable configuration and orientation.

For example, in one embodiment, the edges 58, 59 are curved and at an angle to each other. Although not illustrated, it should be appreciated that in modified embodiments, the ring 55 can be formed without a gap. When the ring 55 is positioned along the inner member 32, the ring 55 preferably surrounds a substantial portion of the inner member 32. The ring 55 can be sized so that the ring 55 can flex or move radially outwardly in response to an axial force so that the ring 55 can be moved relative to the inner member 32. In one embodiment, the tubular housing 56 includes at least one and in the illustrated embodiment four teeth or flanges 60, which are configured to engage the retention structures 40 on the inner member 32. In the illustrated embodiment, the teeth or flanges include a first surface that generally faces the proximal direction and is inclined with respect to the longitudinal axis of the outer sleeve member and a second surface that faces distal direction and lies generally perpendicular to the longitudinal axis of the outer sleeve member. It is contemplated that the teeth or flanges 60 can have any suitable configuration for engaging with the retention structures 40 of the inner member 32.

As with the previous embodiment, the outer sleeve member can includes the annular recess 54 in which the annular ring 55 may be positioned. The body 56 of the ring 55 can be sized to prevent substantial axial movement between the ring 55 and the annular recess 54 (FIG. 9B) during use of the outer sleeve member. In one embodiment, the width of the annular recess 54 in the axial direction is slightly greater than the width of the annular ring 55 in the axial direction. This tolerance between the annular recess 54 and the annular ring 55 can inhibit, or prevent, oblique twisting of the annular ring 55 so that the body 56 of the ring 55 is generally parallel to the outer surface of the inner member 32.

Further, the recess 54 can be sized and dimensioned such that as the outer sleeve member is advanced distally over the inner member 32, the annular ring 55 can slide along the first surface and over the complementary retention structures 40 of the inner member 32. That is, the recess 54 can provide a space for the annular ring 55 to move radially away from the inner member 32 as the outer sleeve member is advanced distally. Of course, the annular ring 55 can be sized and dimensioned such that the ring 55 is biased inwardly to engage the retention structures 40 on the inner member 32. The bias of the annular ring 55 can result in effective engagement between the flanges 60 and the retention structures 40.

A distal portion 61 of the recess 54 can be sized and dimensioned such that after the outer sleeve member 53 is appropriately tensioned the annular ring 55 becomes wedged between the inner member 32 and an angled engagement surface of the distal portion 61. In this manner, proximal movement of the outer sleeve member 53 can be prevented.

FIGS. 9C-9F illustrate another embodiment of an outer sleeve member 53'. In this embodiment, the outer sleeve member 53' includes a recess 54 configured to receive a split ring 55, as described above with reference to FIGS. 9A and 9B. As will be explained in detail below, the outer sleeve member 53' can include an anti-rotation feature to limit or prevent rotation of the ring 55 within the outer sleeve member 53. In light of the disclosure herein, those of skill in the art will recognize various different configurations for limiting the rotation of the ring 55. However, a particularly advantageous arrangement will be described below with reference to the illustrated embodiment.

Figure 9D:
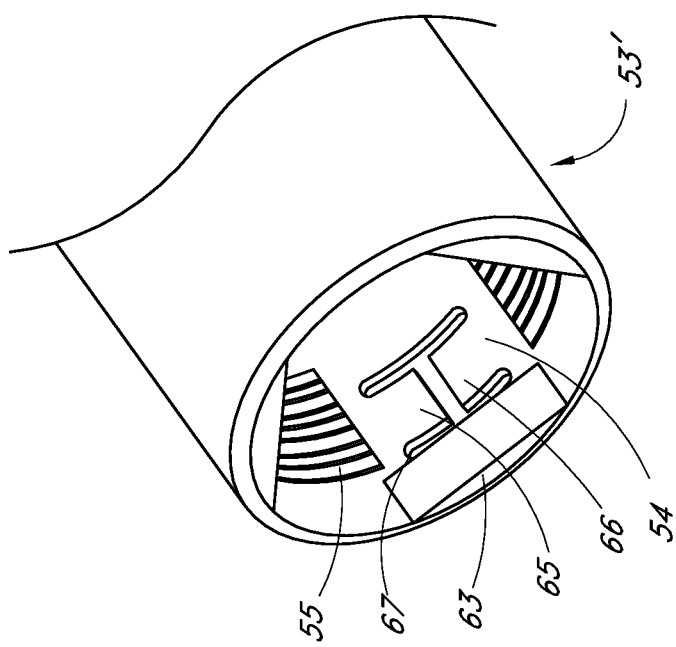
Figure 9F:
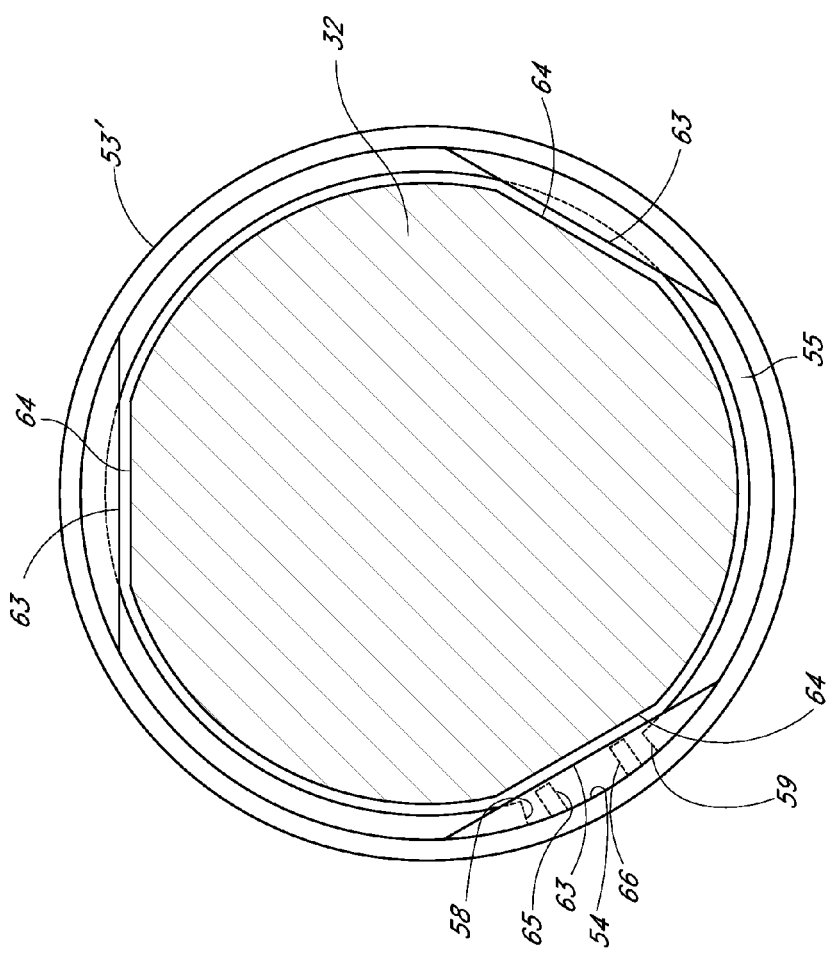
FIG. 9F is a front view of the outer sleeve member shown in FIG. 9C.

In the illustrated embodiment, the outer sleeve member 53' has a tubular housing 62 that can engage with the inner member 32 or the tool 50, as described above. With reference to FIGS. 9D and 9F, the tubular housing 62 can comprise one or more anti-rotational features 63 in the form of a plurality of flat sides that are configured to mate corresponding anti-rotational features 64 or flat sides of the inner member 32 of the actuator shaft 30. As shown in FIG. 9F, in the illustrated embodiment, the inner member 32 has three flat sides 64. Disposed between the flat sides 64 are the portions of the inner member 32 which include the complementary locking structures such as threads or ratchet like structures as described above. The complementary locking structures interact with the ring 55 as described above to resist proximal movement of the outer sleeve member 53' under normal use conditions while permitting distal movement of the outer sleeve member 53' over the inner member 32.

As mentioned above, the ring 55 can be is positioned within the recess 54. In the illustrated embodiment, the recess 54 and ring 55 are positioned near to and proximal of the anti-rotational features 63. However, the ring 55 can be located at any suitable position along the tubular housing 62 such that the ring 55 can interact with the retention features of the inner member 32.

During operation, the ring 55 may rotate to a position such that the gap 57 between the ends 58, 59 of the ring 55 lies above the complementary retention structures on the inner member 32. When the ring 55 is in this position, there is a reduced contact area between the split ring 55 the complementary retention structures thereby reducing the locking strength between the outer sleeve member 53' and the inner member 32. In the illustrated embodiment, for example, the locking strength may be reduced by about ⅓ when the gap 57 over the complementary retention structures between flat sides 64. As such, it is advantageous to position the gap 57 on the flat sides 64 of the inner member 32 that do not include complementary retention structures.

To achieve this goal, the illustrated embodiment includes a pair of tabs 65, 66 that extend radially inward from the interior of the outer sleeve member 53'. The tabs 65, 66 are configured to limit or prevent rotational movement of the ring 55 relative to the housing 62 of the outer sleeve member 53'. In this manner, the gap 57 of the ring 55 may be positioned over the flattened sides 64 of the inner member 32.

In the illustrated embodiment, the tabs 65, 66 have a generally rectangular shape and have a generally uniform thickness. However, it is contemplated that the tabs 65, 66 can be square, curved, or any other suitable shape for engaging with the ring 55 as described herein.

In the illustrated embodiment, the tabs 65, 66 can be formed by making an H-shaped cut 67 in the tubular housing 62 and bending the tabs 65, 66 inwardly as shown in FIG. 9F. As shown in FIG. 9F, the tabs 65, 66 (illustrated in phantom) are interposed between the edges 58, 59 of the ring 55. The edges 58, 59 of the ring 55 can contact the tabs to limit the rotational movement of the ring 55. Those skilled in the art will recognize that there are many suitable manners for forming the tabs 65, 66. In addition, in other embodiments, the tabs 65, 66 may be replaced by a one or more elements or protrusions attached to or formed on the interior of the outer sleeve member 53'.

Referring again to FIGS. 3-6, the actuator shaft 30 can also comprise at least one proximal wedge member 68 being disposed at the proximal end 42 of the outer sleeve member 34. The proximal wedge member 68 can be sized and configured to contact the proximal facing surfaces 18, 20 of the upper and lower body portions 14, 16 upon selective relative movement of the proximal end 42 of the outer sleeve member 34 toward the distal end 36 of the inner member 32. The longitudinal movement of the proximal wedge member 68 against the proximal surfaces 18, 20 can cause the separation of the upper and lower body portions 14, 16 in order to cause the intervertebral implant 10 to expand from the unexpanded state to the expanded state, as shown in FIGS. 5 and 6, respectively.

As illustrated in FIGS. 3-6, the proximal wedge member 68 can be formed separately from the outer sleeve member 34. In such an embodiment, proximal wedge member 68 can be carried on a ring or wedge-type structure that is fitted around or over the outer sleeve member 34. In the illustrated embodiment, the proximal wedge member 68 can taper axially in the distal direction. For example, as shown in FIGS. 3 and 4, the proximal wedge member 68 can have a triangle-like structure that is disposed about the actuator shaft 30 and pushed against the proximal surfaces 18, 20 by the collar 52 of the outer sleeve member 34.

However, in other embodiments, as shown in FIG. 8, the proximal wedge member 68 can also be integrally formed with and/or permanently coupled to the outer sleeve member 34. Such an embodiment can be advantageous in that fewer parts are required, which can facilitate manufacturing and use of the intervertebral implant 10.

Preferably, the proximal surfaces 18, 20 of the upper and lower body portions 14, 16 are configured to substantially match the outer configuration of the proximal wedge member 68. The proximal surfaces 18, 20 can be integrally formed with the upper and lower body portions 14, 16 and have a shape that generally tapers toward the proximal ends 22, 24. The proximal surfaces 18, 20 can be defined by a smooth and constant taper, a non-constant curve, or a contact curve, or other geometries as may be appropriate.

For example, curvature proximal surfaces 18, 20 can be advantageous because initial incremental movement of the proximal wedge member 68 relative to the distal end 36 of the inner member 32 can result in relatively larger incremental distances between the upper and lower body portions 14, 16 than may subsequent incremental movement of the proximal wedge member 68. Thus, these types of adjustments can allow the clinician to quickly expand the intervertebral implant 10 to an initial expanded state with few initial incremental movements, but to subsequently expand the intervertebral implant 10 in smaller and smaller increments in order to fine tune the placement or expanded state of the intervertebral implant 10. Thus, such embodiments can allow the efficiency of the operation to be improved and allow the clinician to fine tune the expansion of the intervertebral implant 10.

With reference to FIGS. 1 and 5, in the illustrated embodiment, the upper and lower body portions 14, 16 can each have distally facing distal surfaces 70, 72 disposed at distal ends 74, 76 thereof, as similarly mentioned above with respect to the proximal surfaces 18, 20. For example, the distal surfaces 70, 72 can be inclined or otherwise curved with respect to the longitudinal axis of the body portions 14, 16. Other features, designs, and configurations of the proximal surfaces 18, 20, as disclosed herein, are not repeated with respect to the distal surfaces 70, 72, but it is understood that such features, designs, and configurations can similarly be incorporated into the design of the distal surfaces 70, 72.

In such an embodiment, the actuator shaft 30 of the intervertebral implant 10 can further comprise at least one distal wedge member 80 that can be disposed at the distal end 36 of the inner member 32. The distal wedge member 80 can be sized and configured to contact the distal surfaces 70, 72 of the respective ones of the upper and lower body portions 14, 16 upon selective relative movement of the distal end 36 of the inner member 32 toward the proximal end 42 of the outer sleeve member 34. As similarly described above with respect to the proximal wedge member 68, the longitudinal movement of the distal wedge member 80 against the distal surfaces 70, 72 can cause the separation of the upper and lower body portions 14, 16 thereby resulting in expansion of the intervertebral implant 10.

The description of the proximal wedge member 68 and its interaction with the proximal surfaces 18, 20, as well as the corresponding structures and embodiments thereof, can likewise be implemented with respect to the distal wedge member 80 and the distal surfaces 70, 72. Therefore, discussion of alternative embodiments, structures, and functions of the distal wedge member 80 and the distal surfaces 70, 72 need not be repeated in detail, but can include those mentioned above with respect to the distal wedge member 80 and the distal surfaces 70, 72.

Figure 11:
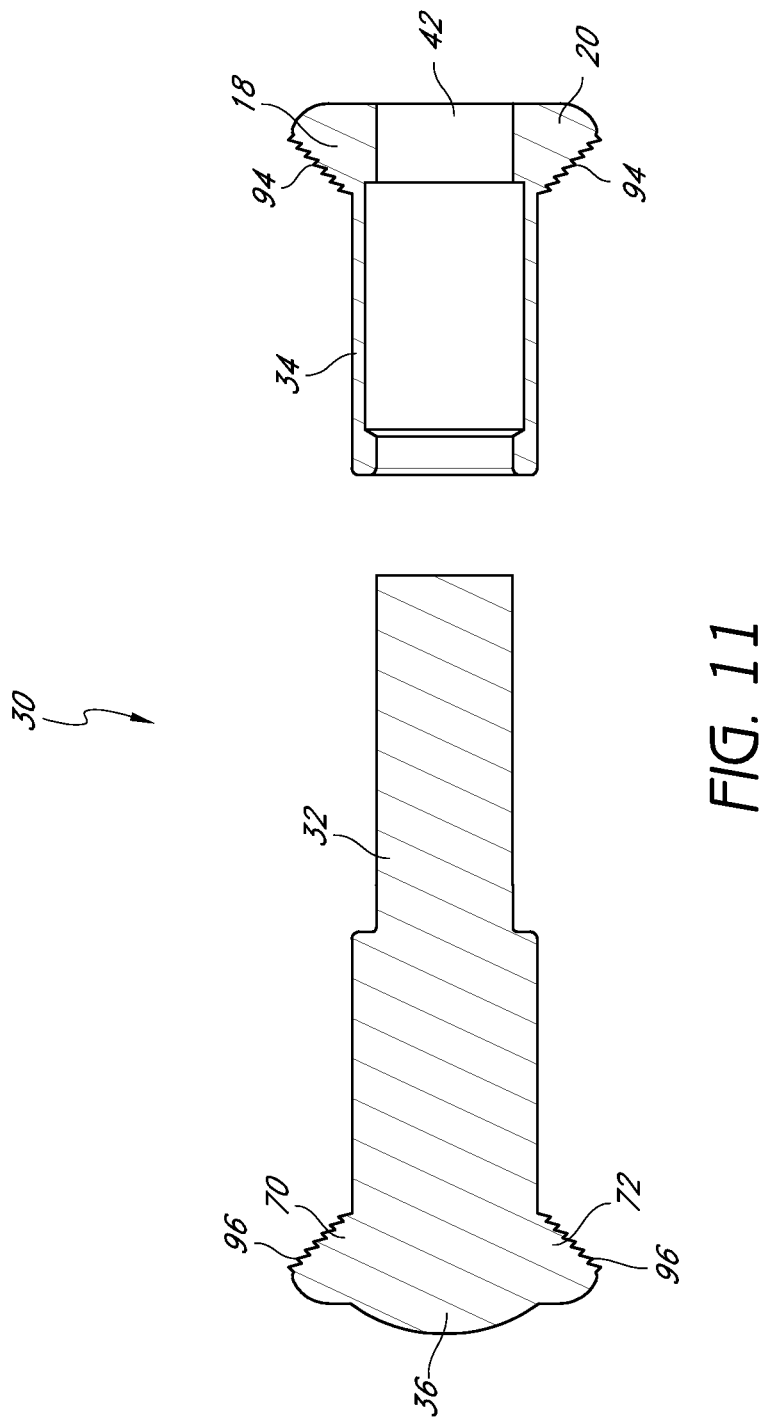
FIG. 11 is a side cross-sectional view of another embodiment of an actuator shaft of the intervertebral implant shown in FIG. 10A.

In accordance with yet another embodiment illustrated in FIGS. 10A-11, at least one of the proximal and distal wedge members 68, 80 can be configured to include engagement surfaces 90, 92. The engagement surfaces 90, 92 can include any variety of surface textures, such as ridges, protrusions, and the like in order to enhance the engagement between the proximal and distal wedge members 68, 80 and the respective ones of the proximal and distal surfaces 18, 20 and 70, 72. In the embodiment illustrated in FIGS. 10A-11, the engagement surfaces 90, 92 can include stepped contours 94, 96, such as comprising a plurality of ridges.

As illustrated in the detail section view of FIG. 10B, the stepped contours 94, 96 of the engagement surfaces 90, 92 can be preferably configured to be inclined or oriented obliquely with respect to the axis of the actuator shaft 30. The use of the engagement surfaces 90, 92 can permit one-way, ratchet type longitudinal movement of proximal and distal wedge members 68, 80 relative to the proximal and distal surfaces 18, 20 and 70, 72 in order to maintain the upper and lower body portions 14, 16 at a given separation distance.

Additionally, at least one of the proximal and distal surfaces 18, 20 and 70, 72 of the upper and lower body portions 14, 16 can include complimentary engagement surfaces 100, 102, 104, 106. The complimentary engagement surfaces 100, 102, 104, 106 can similarly include any variety of surface textures, such as ridges, protrusions, and the like in order to enhance the engagement between the respective ones of the distal and proximal protrusions 68, 80.

In accordance with the embodiment shown in FIGS. 10A-11, the complimentary engagement surfaces 100, 102, 104, 106 can be configured as stepped contours 108, 110 and 112, 114, such as including a plurality of ridges. As shown best in the detail section view of FIG. 10, the stepped contours 108, 110, 112, 114 can also be configured to be inclined or oriented obliquely with respect to the axis of the actuator shaft 30. However, the stepped contours 108, 110, 112, 114 are preferably inclined in a direction opposite to the stepped contours 94, 96 of the proximal and distal wedge members 68, 80.

In such an embodiment, the stepped contours 108, 110, 112, 114 can engage the stepped contours 94, 96 of the wedge members 68, 80 to permit one-way ratcheting of the proximal and distal wedge members 68, 80 along the proximal and distal surfaces 18, 20, 70, 72. This advantageous feature can be incorporated into various embodiments disclosed herein in order to, inter alia, further improve the deployment and stabilization of the intervertebral implant 10.

As shown in FIG. 10A, in this embodiment, the inner member 32 and the outer sleeve member 34 do not include complementary retention structures as described above with reference to FIGS. 3 and 4. Thus, in this embodiment the inner members 32 can be moved with respect to the outer sleeve member 34, and the above-described engagement between the proximal and distal wedge members 68, 80 and the respective ones of the distal and proximal surfaces 18, 20 and 70, 72 can provide ratchet-type movement and maintain expansion of the implant 10. However, in modified embodiments, the retention structures 40, 44 of the actuator shaft 30 can also be provided in addition to the engagement of the proximal and distal wedge members 68, 80 and the respective ones of the proximal and distal surfaces 18, 20 and 70, 72.

Referring again to FIGS. 3 and 4, according to the illustrated embodiment, the intervertebral implant 10 can further comprise at least one alignment guide 120. The alignment guide 120 can be connected to the upper and lower body portions 14, 16 and be operative to facilitate separation of the first and second body portions 14, 16. As shown in FIGS. 3 and 4, the alignment guide 120 can comprise a plurality of guide rods 122 that are disposed through corresponding bores in the upper and lower body portions 14, 16. The rods 122 can be configured to orient the upper body portion 14 substantially orthogonally with respect to an axis of the actuator shaft 30 and with respect to the lower body portion 16. In such an embodiment, the rods 122 can each include a telescoping mechanism to enable and stabilize expansion of the intervertebral implant 30. Preferably, the alignment guide 120 also facilitates expansion or separation of the upper and lower body portions 14, 16 in a direction substantially orthogonal to an axis of the actuator shaft 30, such as in the axial direction of the rods 122.

Figure 12:
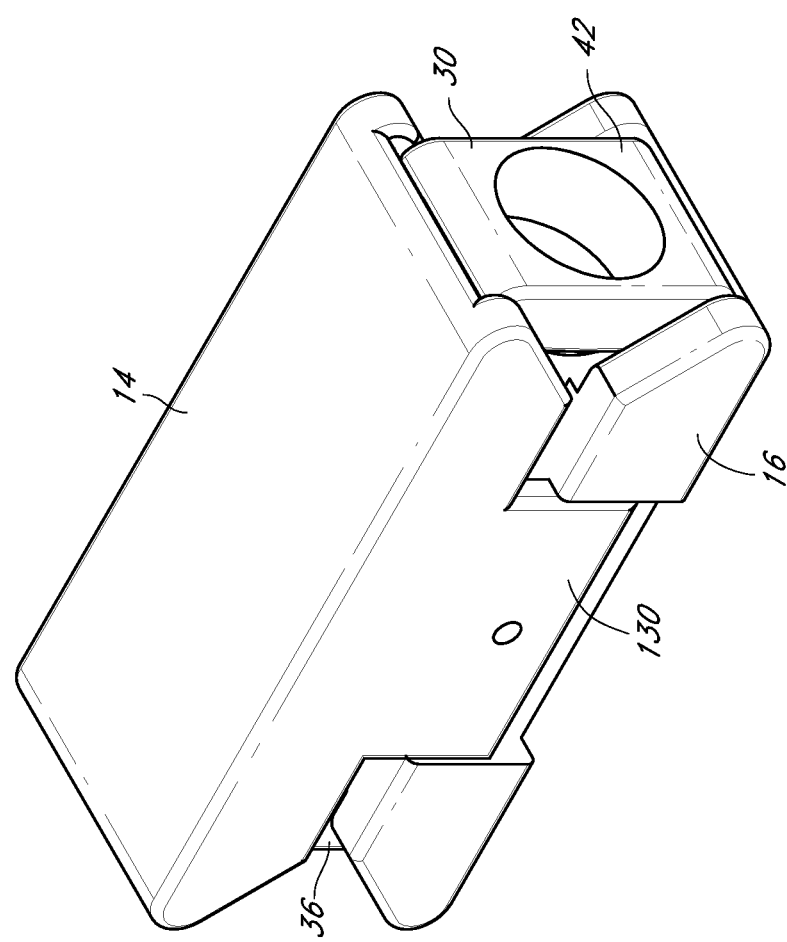
FIG. 12 is a perspective view of the embodiment of the intervertebral implant shown in FIG. 10A in an unexpanded state.
Figure 13:
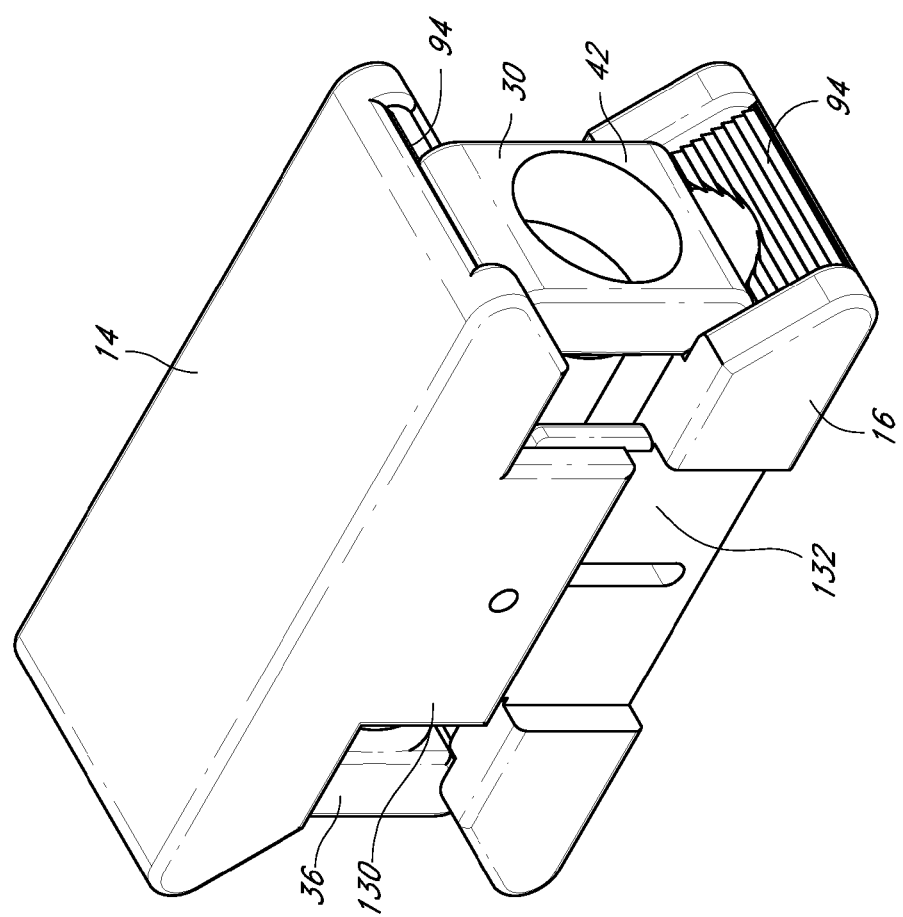
FIG. 13 is a perspective view of the embodiment of the intervertebral implant shown in FIG. 10A in an expanded state.

In accordance with another embodiment illustrated in FIGS. 12 and 13, the alignment guide 120 can also be configured to include a first pair of side rails 130 extending from the upper body portion 14 toward the lower body portion 16 for aligning the upper body portion 14 with the lower body portion 16 to facilitate separation of the upper and lower body portions 14, 16 in a direction substantially orthogonal to an axis of the actuator shaft 30. Further, the alignment guide 120 can also include a second pair of side rails 132 extending from the lower body portion 16 toward the upper body portion 14 for cooperating with the first pair of side rails 130 in aligning the upper body portion 14 with the lower body portion 16 to facilitate separation of the upper and lower body portions 14, 16 in a direction substantially orthogonal to the axis of the actuator shaft 30.

As shown, the first and second pairs of side rails 130, 132 can be configured to extend substantially orthogonally from the respective ones of the upper and lower body portions 14, 16. In this regard, although the upper and lower body portions 14, 16 are illustrated as being configured substantially as parallel plates, any variety of configurations can be provided, such as generally ovular, wedge-shaped, and others, as mentioned above. Thus, the first and second pairs of side rails 130, 132 can be configured accordingly depending upon the configuration and design of the upper and lower body portions 14, 16.

For example, it is contemplated that the first and second pairs of side rails 130, 132 can be configured to ensure that the spacing between the proximal ends 22, 24 of the respective ones of the upper and lower body portions 14, 16 is equal to the spacing between the distal ends 74, 76 thereof. However, the first and second pairs of side rails 130, 132 can also be configured to orient exterior surfaces of the upper and lower body portions 14, 16 at an oblique angle relative to each other. Thus, the spacing between the proximal ends 22, 24 of the respective ones of the upper and lower body portions 14, 16 can be different from the spacing between the distal ends 74, 76 thereof. Thus, in one embodiment, such orientation can be created depending upon the desired configuration of the first and second pairs of side rails 130, 132.

Further, it is contemplated that the first and second pairs of side rails 130, 132 can be linear or planar in shape, as well as to generally conform to the shape of a curve in the longitudinal direction. Furthermore, the first and second pairs of side rails 130, 132 can also be configured to include mating surfaces to facilitate expansion and alignment of the intervertebral implant 10. Finally, the first and second pairs of side rails 130, 132, although illustrated as solid, can include perforations or other apertures to provide circulation through the intervertebral space.

In accordance with yet another embodiment, a method of implanting or installing the spinal fusion implant 10 is also provided. The method can comprise the steps of positioning the intervertebral implant 10 between two vertebral bodies and moving the inner member 32 of the actuator shaft 30 in an proximal direction relative to the outer sleeve member 34 to force the proximal wedge member 68 and distal wedge member 80 against the proximal and distal surfaces 18, 20, 70, 72 of upper and lower body portions 14, 16 of the intervertebral implant 10 to separate the upper and lower body portions 14, 16 to cause the intervertebral implant 10 to expand intermediate the vertebral bodies. The method can be accomplished utilizing the various embodiments as described herein.

For any of the embodiments disclosed above, installation can be simplified through the use of the installation equipment. The installation equipment can comprise a pistol grip or plier-type grip so that the clinician can, for example, position the equipment at the proximal extension of actuator shaft 30, against the proximal end 42 of the outer sleeve member 34, and through one or more contractions with the hand, the proximal end 42 of the outer sleeve member 34 and the distal end 36 of the inner member 32 can be drawn together to appropriately tension.

In particular, while proximal traction is applied to the proximal end 38 of the inner member 32, appropriate tensioning of the actuator shaft 30 is accomplished by tactile feedback or through the use of a calibration device for applying a predetermined load on the actuator shaft 30. Following appropriate tensioning of the actuator shaft 30, the proximal extension of the actuator shaft 30 (or the tool 50) is preferably removed, such as by being unscrewed, cut off or snapped off. Such a cut can be made using conventional saws, cutters or bone forceps which are routinely available in the clinical setting.

In certain embodiments, the proximal extension of the actuator shaft 30 may be removed by cauterizing. Cauterizing the proximal extension may advantageously fuse the proximal end 38 of the inner member 32 to the distal end 42 of the outer sleeve member 34, thereby adding to the retention force between the outer sleeve member 34 and the inner member 30 and between the proximal and distal protrusions 68, 80 and the respective ones of the distal and proximal surfaces 18, 20 and 70, 72, if applicable. Such fusion between the proximal end 38 of the inner member 32 to the distal end 42 of the outer sleeve member 34 may be particularly advantageous if the intervertebral implant 10 is made from a bioabsorbable and/or biodegradable material. In this manner, as the material of the proximal anchor and/or the actuator shaft is absorbed or degrades, the fusion caused by the cauterizing continues to provide retention force between the proximal anchor and the pin.

Following trimming the proximal end of actuator shaft 30, the access site may be closed and dressed in accordance with conventional wound closure techniques.

Preferably, the clinician will have access to an array of intervertebral implants 10, having different widths and axial lengths. These may be packaged one or more per package in sterile envelopes or peelable pouches. Upon encountering an intervertebral space for which the use of a intervertebral implant 10 is deemed appropriate, the clinician will assess the dimensions and load requirements of the spine 12, and select an intervertebral implant 10 from the array which meets the desired specifications.

The embodiments described above may be used in other anatomical settings beside the spine. As mentioned above, the embodiments described herein may be used for spinal fixation. In embodiments optimized for spinal fixation in an adult human population, the upper and lower portions 14, 15 will generally be within the range of from about 10-60 mm in length and within the range of from about 5-30 mm in maximum width and the device can expand from a height of about 5 mm to about 30 mm.

For the embodiments discussed herein, the intervertebral implant components can be manufactured in accordance with any of a variety of techniques which are well known in the art, using any of a variety of medical-grade construction materials. For example, the upper and lower body portions 14, 16, the actuator shaft 30, and other components can be injection-molded from a variety of medical-grade polymers including high or other density polyethylene, PEEK™ polymers, nylon and polypropylene. Retention structures 40, 44 can also be integrally molded with the actuator shaft 30. Alternatively, retention structures 40, 44 can be machined or pressed into the actuator shaft 30 in a post-molding operation, or secured using other techniques depending upon the particular design. The retention structures 40, 44 can also be made of a different material.

The intervertebral implant 10 components can be molded, formed or machined from biocompatible metals such as Nitinol, stainless steel, titanium, and others known in the art. Non-metal materials such as plastics, PEEK™ polymers, and rubbers can also be used. Further, the implant components can be made of combinations of PEEK™ polymers and metals. In one embodiment, the intervertebral implant components can be injection-molded from a bioabsorbable material, to eliminate the need for a post-healing removal step.

The intervertebral implant components may contain one or more bioactive substances, such as antibiotics, chemotherapeutic substances, angiogenic growth factors, substances for accelerating the healing of the wound, growth hormones, antithrombogenic agents, bone growth accelerators or agents, and the like. Such bioactive implants may be desirable because they contribute to the healing of the injury in addition to providing mechanical support.

In addition, the intervertebral implant components may be provided with any of a variety of structural modifications to accomplish various objectives, such as osteoincorporation, or more rapid or uniform absorption into the body. For example, osteoincorporation may be enhanced by providing a micropitted or otherwise textured surface on the intervertebral implant components. Alternatively, capillary pathways may be provided throughout the intervertebral implant, such as by manufacturing the intervertebral implant components from an open cell foam material, which produces tortuous pathways through the device. This construction increases the surface area of the device which is exposed to body fluids, thereby generally increasing the absorption rate. Capillary pathways may alternatively be provided by laser drilling or other technique, which will be understood by those of skill in the art in view of the disclosure herein. Additionally, apertures can be provided in the implant to facilitate packing of biologics into the implant, backfilling, and/or osseointegration of the implant. In general, the extent to which the intervertebral implant can be permeated by capillary pathways or open cell foam passageways may be determined by balancing the desired structural integrity of the device with the desired reabsorption time, taking into account the particular strength and absorption characteristics of the desired polymer.

The intervertebral implant may be sterilized by any of the well known sterilization techniques, depending on the type of material. Suitable sterilization techniques include heat sterilization, radiation sterilization, such as cobalt irradiation or electron beams, ethylene oxide sterilization, and the like.

Referring now to FIGS. 14A-14D, various modified configurations and applications of the implant are illustrated. As mentioned above, the embodiments, applications, and arrangements disclosed herein can be readily modified by one of skill in order to suit the requirements of the clinician. It will therefore be appreciated that embodiments disclosed herein are not limited to those illustrated, but can be combined and/or modified.

Figure 14C:
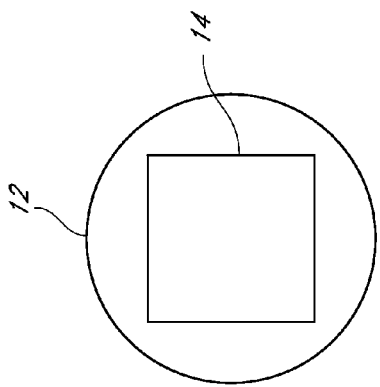
FIG. 14C is a top view of another embodiment of the intervertebral implant wherein the upper and lower body portions have generally square upper and lower faces.
Figure 14D:
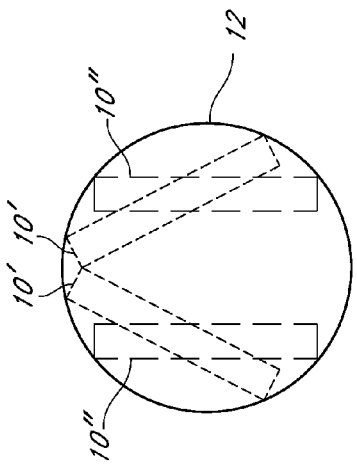
FIG. 14D is a top view illustrating an embodiment of an application of the intervertebral implant utilizing a plurality of intervertebral implants disposed in an intervertebral space to support adjacent vertebrae.
Figure 14A:
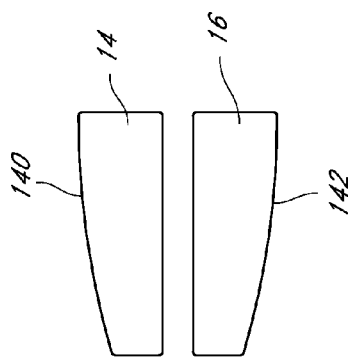
FIG. 14A is a side view of another embodiment of the intervertebral implant wherein the upper and lower body portions have generally slanted configurations.

FIG. 14A is a side view of another embodiment of an intervertebral implant 10 wherein the upper and lower body portions 14, 16 have generally slanted configurations. As illustrated, the upper and lower body portions 14, 16 can define generally convex upper and lower surfaces 140, 142, respectively. Such an embodiment can be beneficial especially in applications where the implant 10 must complement the natural curvature of the spine. The upper and lower surfaces 140, 142 can generally match the concavity of adjacent upper and lower vertebral bodies. It will be appreciated that the slanted configuration can be modified and a range of curvatures can be accommodated as required. Furthermore, the upper and lower surfaces 140, 142 can be generally planar and oriented at an angle relative to each other. In some embodiments, the upper and lower surfaces 140, 142 of the implant 10 can be formed such that the implant defines a generally wedge-shaped design. The dimensions of the implant 10 can be varied as desired.

As illustrated in FIG. 14A, the upper and lower body portions 14, 16 can be configured such that exterior surfaces thereof are oriented obliquely with respect to interior surfaces thereof. For example, in some embodiments, the upper and lower body portions 14, 16 can be configured generally as wedges. However, as also mentioned with regard to FIGS. 12 and 13, it is also contemplated that the actuation mechanism of the implant can allow the spacing between the proximal ends of the respective ones of the upper and lower body portions to be different from of the spacing between the distal ends thereof due to the overall configuration of the implant.

In this regard, the angular relationship between the upper and lower body portions 14, 16 can be varied as desired. For example, the spacing of the distal ends of the upper and lower body portions 14, 16 can increase at a greater rate as the implant is expanded that the spacing between the proximal ends of the upper and lower body portions 14, 16, or vice versa. This feature can result from the interaction of the actuator shaft with the implant, the wedges with the upper and lower body portions 14, 16, or the actuator shaft with the wedges. It is contemplated, for example, that the distal and proximal wedges can have different configurations with different angular relationships between their contact surfaces. Further, the actuator shaft can have different thread configurations such that one wedge advances faster than the other wedge upon rotation of the pin. Alternative embodiments can also be developed based on the present disclosure.

Figure 14B:
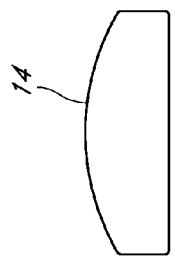
FIG. 14B is a top view of another embodiment of the intervertebral implant wherein the upper and lower body portions have semicircular upper and lower faces.

Referring now to FIG. 14B, a top view of another embodiment of an intervertebral implant 10 is provided wherein the implant 10 has a generally clamshell configuration. Such an embodiment can be beneficial in applications where the clinician desires to support the vertebrae principally about their peripheral aspects.

For example, at least one of the upper and lower body portions 14, 16 can be configured to have a semicircular face. When such an embodiment is implanted and deployed in a patient, the outwardly bowed portions of the upper and lower body portions 14, 16 provide a footprint that allows the implant 10 to contact the vertebrae about their periphery, as opposed to merely supporting the vertebrae in a substantially central or axial location. In such embodiments, the upper and lower body portions 14, 16 can thus be banana or crescent shaped to facilitate contact with cortical bone. Thus, such embodiments can employ the more durable, harder structure of the periphery of the vertebrae to support the spine.

In an additional embodiment, FIG. 14C shows a top view of an intervertebral implant 10 illustrating that the implant 10 can have a generally square configuration and footprint when implanted into the intervertebral space of the spine 12. Such a configuration would likely be utilized in a more invasive procedure, rather than in percutaneous applications. As mentioned above with respect to FIG. 14B, the footprint of such an embodiment can allow the implant 10 to more fully contact the more durable, harder portions of the vertebrae to facilitate support and healing of the spine. Alternative embodiments can be created that provide ovular, circular, hexagonal, rectangular, and any other shaped footprint.

Furthermore, FIG. 14D is a top view of the spine 12 illustrating an exemplary application of the intervertebral implant. In this example, a plurality of intervertebral implants 10' and 10" (shown in hidden lines) can be disposed in an intervertebral space of the spine 12 to support adjacent vertebrae. As mentioned above, one of the beneficial aspects of embodiments of the implant provides that the implant can be used in percutaneous applications.

In FIG. 14D, it is illustrated that one or more implants 10' can be implanted and oriented substantially parallel with respect to each other in order to support the adjacent vertebrae. Also shown, at least two implants 10" can be implanted and oriented transversely with respect to each other in order to support the adjacent vertebrae. In addition, it is contemplated that a cross-midline approach can be used wherein a single implant is placed into the intervertebral space in an orientation as depicted for one of the implants 10', although more centrally. Thus, the angular orientation of the implant(s) can be varied. Further, the number of implants used in the spinal fusion procedure can also be varied to include one or more. Other such configurations, orientations, and operational parameters are contemplated in order to aid the clinician in ensuring that the adjacent vertebrae are properly supported, and that such procedure is performed in a minimally invasive manner.

Figure 15:
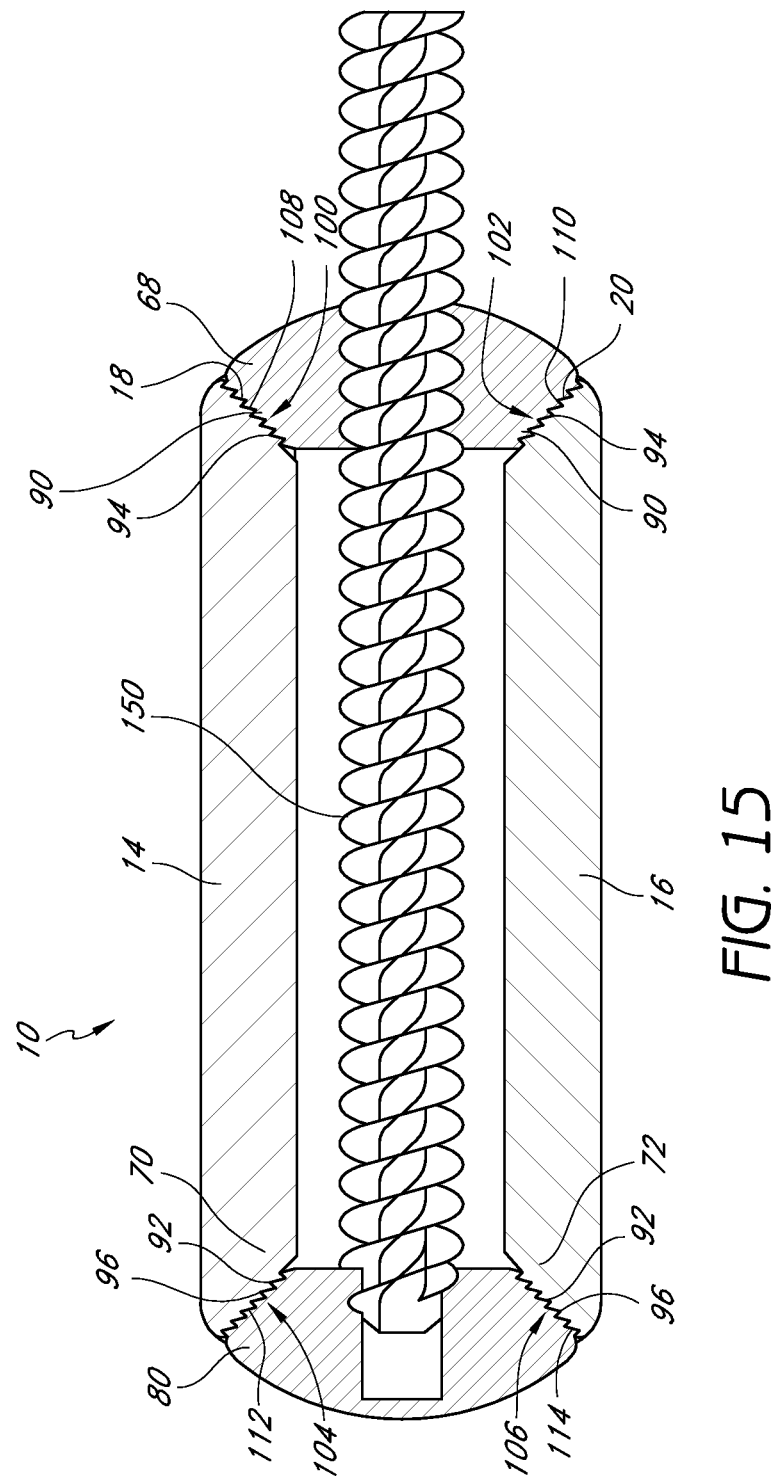
FIG. 15 is a side cross-sectional view of another embodiment of the intervertebral implant wherein rotational movement can be utilized to expand the implant.

Referring now to FIG. 15, yet another embodiment is provided. FIG. 15 is a side view of an intervertebral implant 10 in an unexpanded state in which a screw mechanism 150 can be utilized to draw the proximal and distal wedged members 68, 80 together to cause the implant to move to an expanded state. Thus, a rotational motion, instead of a translational motion (as discussed above in reference to other embodiments) can be utilized to cause the implant 10 to move to its expanded state.

In some embodiments, the screw mechanism 150 can comprise an Archimedes screw, a jack bolt, or other fastener that can cause the convergence of two elements that are axially coupled to the fastener. The screw mechanism 150 can have at least one thread disposed along at least a portion thereof, if not along the entire length thereof. Further, the screw mechanism can be threadably attached to one or both of the proximal and distal wedge members 68, 80. As illustrated in FIG. 15, the distal wedge member 80 can also be freely rotatably attached to the screw mechanism 150 while the proximal wedge member 68 is threadably attached thereto. Further, as disclosed above with respect to the pin, the screw mechanism 150 can also be configured such that a proximal portion of the screw mechanism 150 can be removed after the implant 10 has been expanded in order to eliminate any proximal protrusion of the screw mechanism 150.

Therefore, in the illustrated embodiment, it is contemplated that upon rotation of the screw mechanism 150, the proximal and distal wedged members 68, 80 can be axially drawn closer together. As a result of this axial translation, the proximal and distal wedged members 68, 80 can contact the respective ones of the proximal and distal surfaces 18, 20 and 70, 72 in order to facilitate separation of the upper and lower body portions 14, 16, as similarly disclosed above.

The screw mechanism 150 can be utilized to provide a stabilizing axial force to the proximal and distal wedge members 68, 80 in order to maintain the expansion of the implant 10. However, it is also contemplated that other features can be incorporated into such an embodiment to facilitate the maintenance of the expansion. In this regard, although the axial force provided by the screw mechanism 150 can tend to maintain the position and stability of the proximal and distal wedge members 68, 80, additional features can be employed to ensure the strength and stability of the implant 10 when in its expanded state.

For example, as discussed above with respect to FIGS. 10A-10B, the proximal and distal wedge members 68, 80 can include engagement surfaces 90, 92, such as stepped contours 94, 96. As discussed above, the use of the engagement surfaces 90, 92 can permit one-way, ratchet type longitudinal movement of proximal and distal wedge members 68, 80 relative to the proximal and distal surfaces 18, 20 and 70, 72 in order to maintain the upper and lower body portions 14, 16 at a given separation distance.

Furthermore, as also disclosed above, at least one of the proximal and distal surfaces 18, 20 and 70, 72 of the upper and lower body portions 14, 16 can include complimentary engagement surfaces 100, 102, 104, 106 to enhance the engagement between the respective ones of the distal and proximal protrusions 68, 80. In an embodiment, the complimentary engagement surfaces 100, 102, 104, 106 can be configured as stepped contours 108, 110 and 112, 114. Thus, the stepped contours 108, 110, 112, 114 can engage the stepped contours 94, 96 of the wedge members 68, 80 to permit one-way ratcheting of the proximal and distal wedge members 68, 80 along the proximal and distal surfaces 18, 20, 70, 72.

Therefore, some embodiments can be configured such that a rotational motion can be exerted on the actuator shaft or screw mechanism, instead of a pulling or translational motion, in order to expand an embodiment of the implant from an unexpanded state (such as that illustrated in FIG. 12) to an expanded state (such as that illustrated in FIG. 13). Such embodiments can be advantageous in certain clinical conditions and can provide the clinician with a variety of options for the benefit of the patient. Further, the various advantageous features discussed herein with respect to other embodiments can also be incorporated into such embodiments.

Figure 16A:
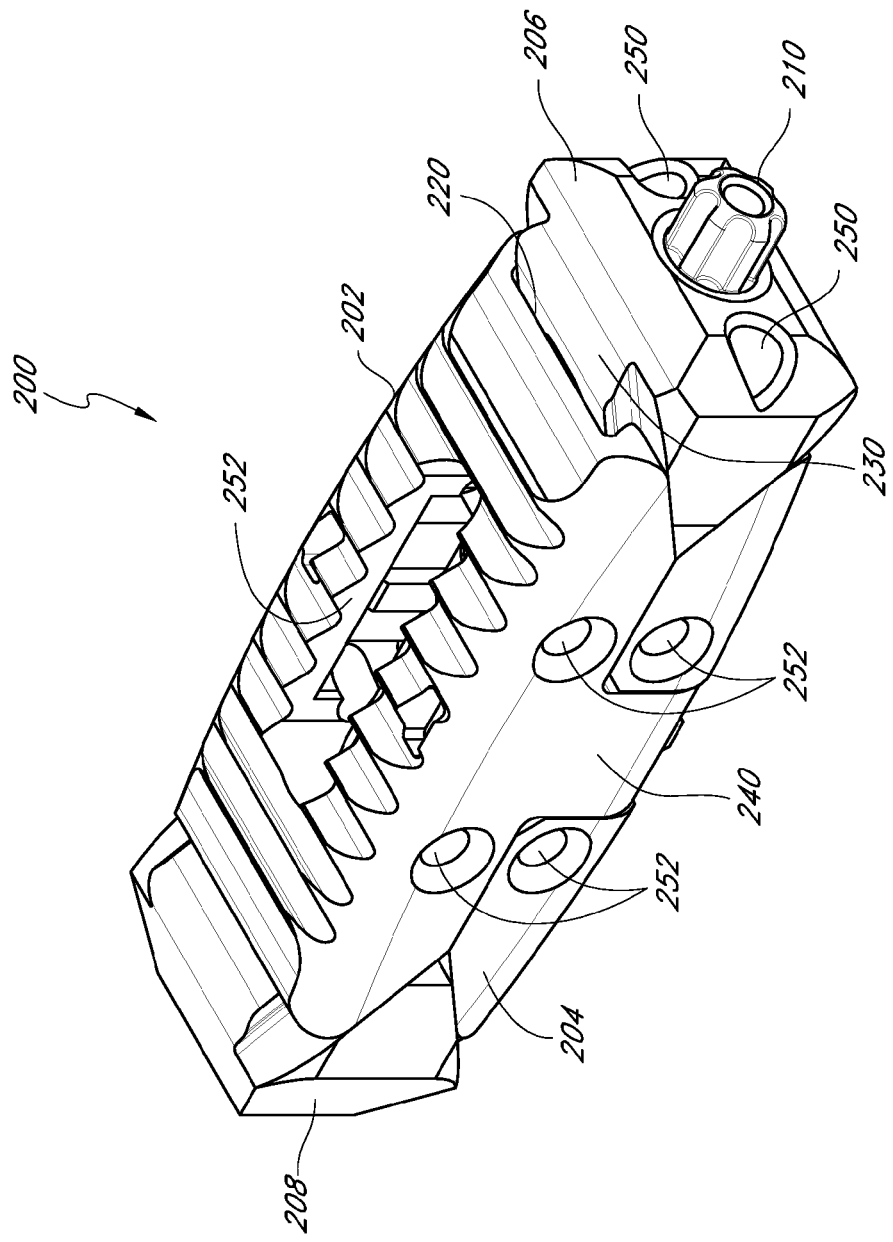
FIG. 16A is a perspective view of another embodiment of an intervertebral implant in an unexpanded state.

Referring now to FIG. 16A-19, another embodiment of the implant is illustrated. FIG. 16A is a perspective view of an intervertebral implant 200 in an unexpanded state. The implant 200 can comprise upper and lower body portions 202, 204, proximal and distal wedge members 206, 208, and an actuator shaft 210. In the unexpanded state, the upper and lower body portions 202, 204 can be generally abutting with a height of the implant 200 being minimized. However, the implant 200 can be expanded, as shown in FIG. 16B to increase the height of the implant 200 when implanted into the intervertebral space of the spine.

In some embodiments, the height of the implant 200 can be between approximately 7-15 mm, and more preferably, between approximately 8-13 mm. The width of the implant can be between approximately 7-11 mm, and preferably approximately 9 mm. The length of the implant 200 can be between approximately 18-30 mm, and preferably approximately 22 mm. Thus, the implant 200 can have a preferred aspect ratio of between approximately 7:11 and 15:7, and preferably approximately between 8:9 and 13:9. It is contemplated that various modifications to the dimension disclosed herein can be made by one of skill and the mentioned dimensions shall not be construed as limiting.

Additionally, as noted above, the implant 200 can also be made using non-metal materials such as plastics, PEEK™ polymers, and rubbers. Further, the implant components can be made of combinations of PEEK™ polymers and metals. Accordingly, the implant 200 can be at least partially radiolucent, which radiolucency can allow a doctor to perceive the degree of bone growth around and through the implant. The individual components of the implant 200 can be fabricated of such materials based on needed structural, biological and optical properties.

As discussed generally above with respect to FIG. 15, it is contemplated that the actuator shaft 210 can be rotated to cause the proximal and distal wedge members to move toward each other, thus causing the upper and lower body portions 202, 204 to be separated. Although, the present embodiment is illustrated using this mode of expansion, it is contemplated that other modes of expansion described above (e.g., one way-ratchet type mechanism) can be combined with or interchanged herewith.

In some embodiments, the implant 200 can be configured such that the proximal and distal wedge members 206, 208 are interlinked with the upper and lower body portions 202, 204 to improve the stability and alignment of the implant 200.

Figure 16B:
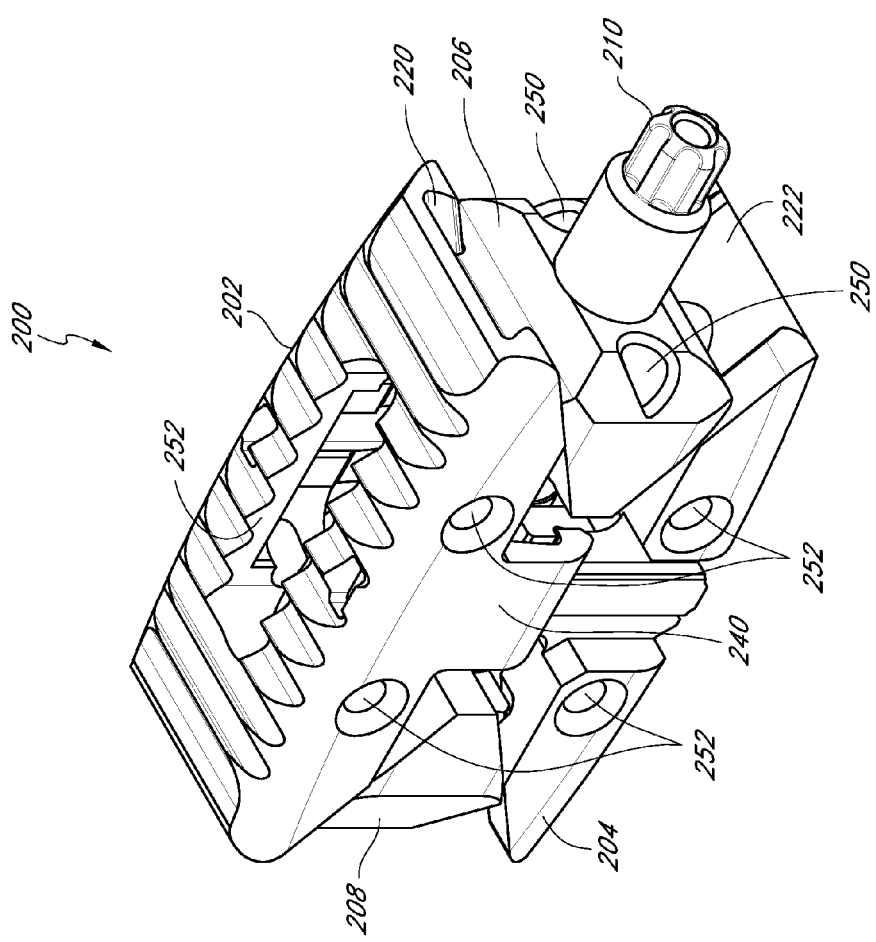
FIG. 16B is a perspective view of the intervertebral implant shown in FIG. 16A wherein the implant is in an expanded state.
Figure 18:
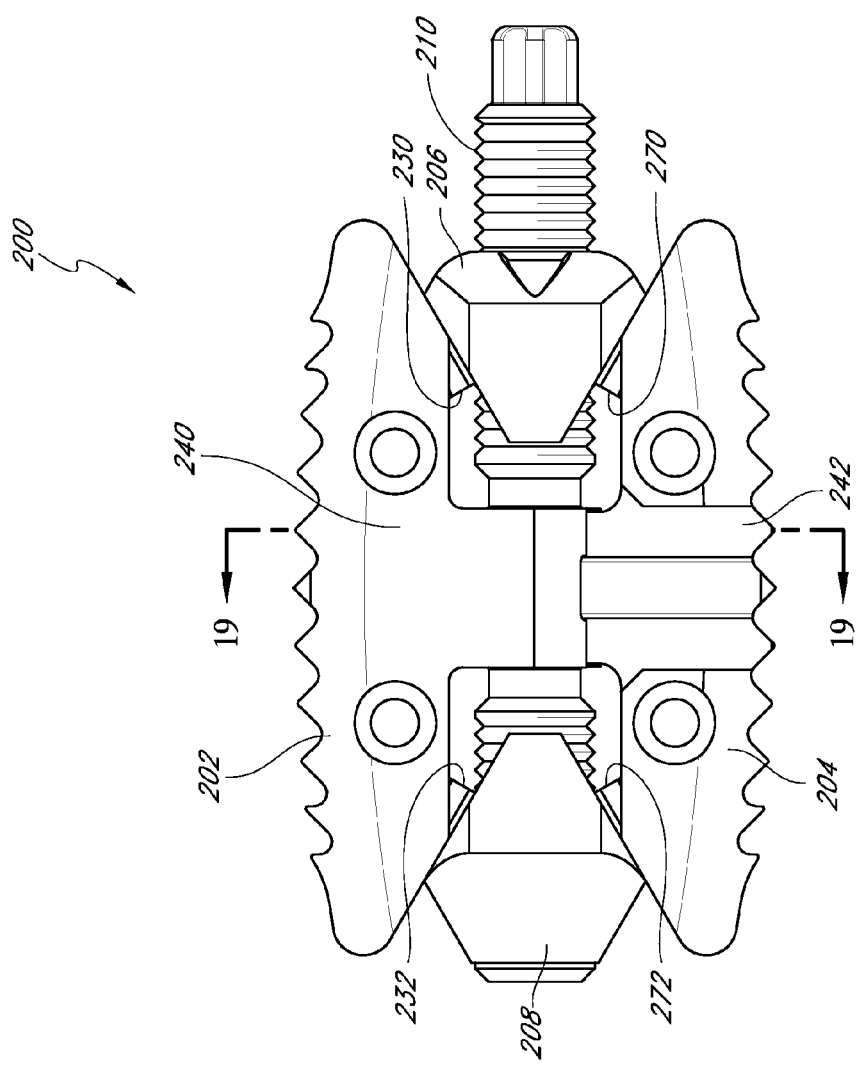
FIG. 18 is a side view of the intervertebral implant shown in FIG. 16B.
Figure 19:
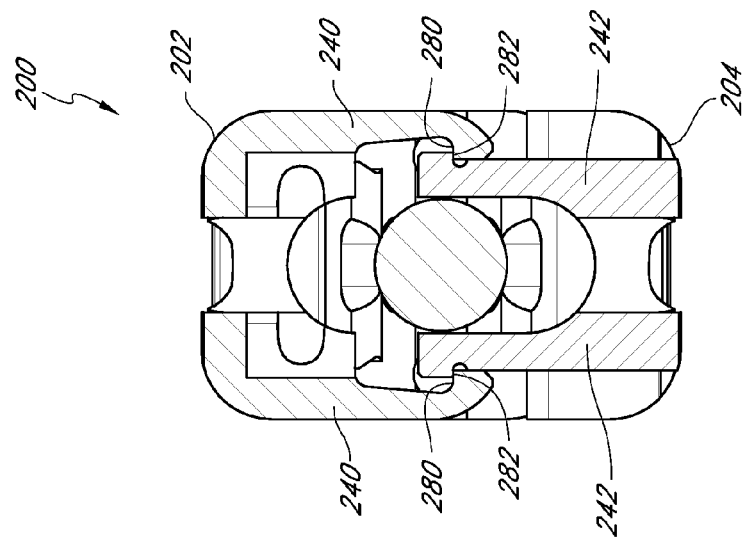
FIG. 19 is a front cross-sectional view of the intervertebral implant shown in FIG. 16B taken along lines 19-19.

For example, the upper and lower body portions 202, 204 can be configured to include slots (slot 220 is shown in FIG. 16A, and slots 220, 222 are shown in FIG. 16B; the configuration of such an embodiment of the upper and lower body portions 202, 204 is also shown in FIGS. 20A-21B, discussed below). In such an embodiment, the proximal and distal wedge members 206, 208 can be configured to include at least one guide member (an upper guide member 230 of the proximal wedge member 206 is shown in FIG. 16A and an upper guide member 232 of the distal wedge member 208 is shown in FIG. 18) that at least partially extends into a respective slot of the upper and lower body portions. The arrangement of the slots and the guide members can enhance the structural stability and alignment of the implant 200.

In addition, it is contemplated that some embodiments of the implant 200 can be configured such that the upper and lower body portions 202, 204 each include side portions (shown as upper side portion 240 of the upper body portion 202 and lower side portion 242 of the lower body portion 204) that project therefrom and facilitate the alignment, interconnection, and stability of the components of the implant 200. FIG. 16B is a perspective view of the implant 200 wherein the implant 200 is in the expanded state. The upper and lower side portions 240, 242 can be configured to have complementary structures that enable the upper and lower body portions 202, 204 to move in a vertical direction. Further, the complementary structures can ensure that the proximal ends of the upper and lower body portions 202, 204 generally maintain spacing equal to that of the distal ends of the upper and lower body portions 202, 204. The complementary structures are discussed further below with regard to FIGS. 17-21B.

Furthermore, as described further below, the complementary structures can also include motion limiting portions that prevent expansion of the implant beyond a certain height. This feature can also tend to ensure that the implant is stable and does not disassemble during use.

In some embodiments, the actuator shaft 210 can facilitate expansion of the implant 200 through rotation, longitudinal contract of the pin, or other mechanisms. The actuator shaft 210 can include threads that threadably engage at least one of the proximal and distal wedge members 206, 208. The actuator shaft 210 can also facilitate expansion through longitudinal contraction of the actuator shaft as proximal and distal collars disposed on inner and outer sleeves move closer to each other to in turn move the proximal and distal wedge members closer together, as described above with respect to actuator shaft 30 shown in FIGS. 5-6. It is contemplated that in other embodiments, at least a portion of the actuator shaft can be axially fixed relative to one of the proximal and distal wedge members 206, 208 with the actuator shaft being operative to move the other one of the proximal and distal wedge members 206, 208 via rotational movement or longitudinal contraction of the pin.

Further, in embodiments wherein the actuator shaft 210 is threaded, it is contemplated that the actuator shaft 210 can be configured to bring the proximal and distal wedge members closer together at different rates. In such embodiments, the implant 200 could be expanded to a V-configuration or wedged shape. For example, the actuator shaft 210 can comprise a variable pitch thread that causes longitudinal advancement of the distal and proximal wedge members at different rates. The advancement of one of the wedge members at a faster rate than the other could cause one end of the implant to expand more rapidly and therefore have a different height that the other end. Such a configuration can be advantageous depending on the intervertebral geometry and circumstantial needs.

In other embodiments, the implant 200 can be configured to include anti-torque structures 250. The anti-torque structures 250 can interact with at least a portion of a deployment tool during deployment of the implant to ensure that the implant maintains its desired orientation (see FIGS. 25-26 and related discussion). For example, when the implant 200 is being deployed and a rotational force is exerted on the actuator shaft 210, the anti-torque structures 250 can be engaged by a non-rotating structure of the deployment tool to maintain the rotational orientation of the implant 200 while the actuator shaft 210 is rotated. The anti-torque structures 250 can comprise one or more inwardly extending holes or indentations on the proximal wedge member 206, which are shown as a pair of holes in FIGS. 16A-B. However, the anti-torque structures 250 can also comprise one or more outwardly extending structures.

According to yet other embodiments, the implant 200 can be configured to include one or more apertures 252 to facilitate osseointegration of the implant 200 within the intervertebral space. As mentioned above, the implant 200 may contain one or more bioactive substances, such as antibiotics, chemotherapeutic substances, angiogenic growth factors, substances for accelerating the healing of the wound, growth hormones, antithrombogenic agents, bone growth accelerators or agents, and the like. Indeed, various biologics can be used with the implant 200 and can be inserted into the disc space or inserted along with the implant 200. The apertures 252 can facilitate circulation and bone growth throughout the intervertebral space and through the implant 200. In such implementations, the apertures 252 can thereby allow bone growth through the implant 200 and integration of the implant 200 with the surrounding materials.

FIG. 17 is a bottom view of the implant 200 shown in FIG. 16A. As shown therein, the implant 200 can comprise one or more protrusions 260 on a bottom surface 262 of the lower body portion 204. Although not shown in this FIG., the upper body portion 204 can also define a top surface having one or more protrusions thereon. The protrusions 260 can allow the implant 200 to engage the adjacent vertebrae when the implant 200 is expanded to ensure that the implant 200 maintains a desired position in the intervertebral space.

The protrusions 260 can be configured in various patterns. As shown, the protrusions 260 can be formed from grooves extending widthwise along the bottom surface 262 of the implant 200 (also shown extending from a top surface 264 of the upper body portion 202 of the implant 200). The protrusions 260 can become increasingly narrow and pointed toward their apex. However, it is contemplated that the protrusions 260 can be one or more raised points, cross-wise ridges, or the like.

FIG. 17 also illustrates a bottom view of the profile of an embodiment of the upper side portion 240 and the profile of the lower side portion 242. As mentioned above, the upper and lower side portions 240, 242 can each include complementary structures to facilitate the alignment, interconnection, and stability of the components of the implant 200. FIG. 17 also shows that in some embodiments, having a pair of each of upper and lower side portions 240, 242 can ensure that the upper and lower body portions 202, 204 do not translate relative to each other, thus further ensuring the stability of the implant 200.

As illustrated in FIG. 17, the upper side portion 240 can comprise a groove 266 and the lower side portion can comprise a rib 268 configured to generally mate with the groove 266. The groove 266 and rib 268 can ensure that the axial position of the upper body portion 202 is maintained generally constant relative to the lower body portion 204. Further, in this embodiment, the grooves 266 and rib 268 can also ensure that the proximal ends of the upper and lower body portions 202, 204 generally maintain spacing equal to that of the distal ends of the upper and lower body portions 202, 204. This configuration is also illustratively shown in FIG. 18.

Referring again to FIG. 17, the implant 200 is illustrated in the unexpanded state with each of the respective slots 222 of the lower body portion 204 and lower guide members 270, 272 of the respective ones of the proximal and distal wedge members 206, 208. In some embodiments, as shown in FIGS. 16A-17 and 19-21B, the slots and guide members can be configured to incorporate a generally dovetail shape. Thus, once a given guide member is slid into engagement with a slot, the guide member can only slide longitudinally within the slot and not vertically from the slot. This arrangement can ensure that the proximal and distal wedge members 206, 208 are securely engaged with the upper and lower body portions 202, 204.

Furthermore, in FIG. 18, a side view of the embodiment of the implant 200 in the expanded state illustrates the angular relationship of the proximal and distal wedge members 206, 208 and the upper and lower body portions 202, 204. As mentioned above, the dovetail shape of the slots and guide members ensures that for each given slot and guide member, a given wedge member is generally interlocked with the give slot to only provide one degree of freedom of movement of the guide member, and thus the wedge member, in the longitudinal direction of the given slot.

Accordingly, in such an embodiment, the wedge members 206, 208 may not be separable from the implant when the implant 200 is in the unexpanded state (as shown in FIG. 16A) due to the geometric constraints of the angular orientation of the slots and guide members with the actuator shaft inhibiting longitudinal relative movement of the wedge members 206, 208 relative to the upper and lower body portions 202, 204. Such a configuration ensures that the implant 200 is stable and structurally sound when in the unexpanded state or during expansion thereof, thus facilitating insertion and deployment of the implant 200.

Such an embodiment of the implant 200 can therefore be assembled by placing or engaging the wedge members 206, 208 with the actuator shaft 210, moving the wedge members 206, 208 axially together, and inserting the upper guide members 230, 232 into the slots 220 of the upper body portion 202 and the lower guide members 270, 272 into the slots 222 of the lower body portion 204. The wedge members 206, 208 can then be moved apart, which movement can cause the guide members and slots to engage and bring the upper and lower body portions toward each other. The implant 200 can then be prepared for insertion and deployment by reducing the implant 200 to the unexpanded state.

During assembly of the implant 200, the upper and lower body portions 202, 204 can be configured to snap together to limit expansion of the implant 200. For example, the upper and lower side portions 240, 242 can comprise upper and lower motion-limiting structures 280, 282, as shown in the cross-sectional view of FIG. 19. After the wedge members 206, 208 are engaged with the upper and lower body portions 202, 204 and axially separated to bring the upper and lower body portions 202, 204 together, the upper motion-limiting structure 280 can engage the lower motion-limiting structure 282. This engagement can occur due to deflection of at least one of the upper and lower side portions 240, 242. However, the motion-limiting structures 280, 282 preferably comprise interlocking lips or shoulders to engage one another when the implant 200 has reached maximum expansion. Accordingly, after the wedge members 206, 208 are assembled with the upper and lower body portions 202, 204, these components can be securely interconnected to thereby form a stable implant 200.

Referring again to FIG. 18, the implant 200 can define generally convex top and bottom surfaces 264, 262. This shape, as discussed above with respect to FIG. 14A, can be configured to generally match the concavity of adjacent vertebral bodies.

Figure 21B:
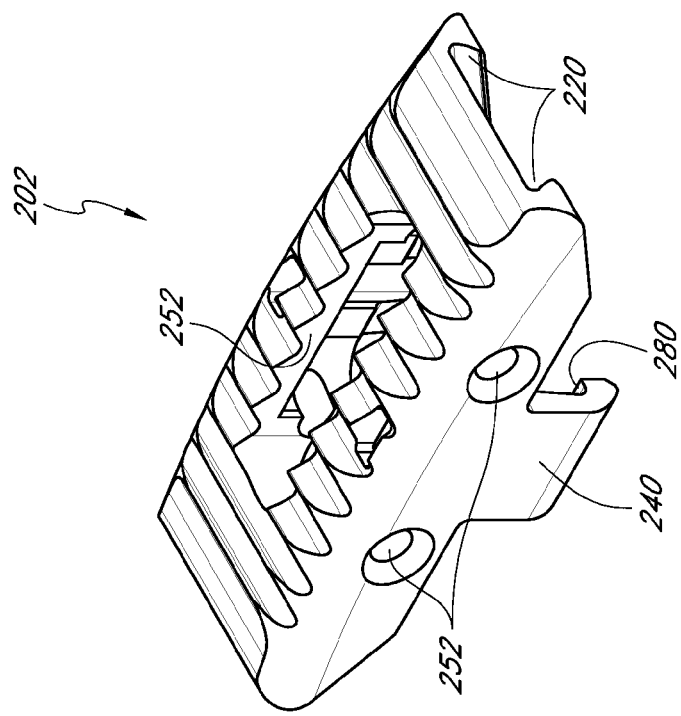
FIG. 21B is a top perspective view of the upper body portion of the intervertebral implant shown in FIG. 16A.
Figure 21A:
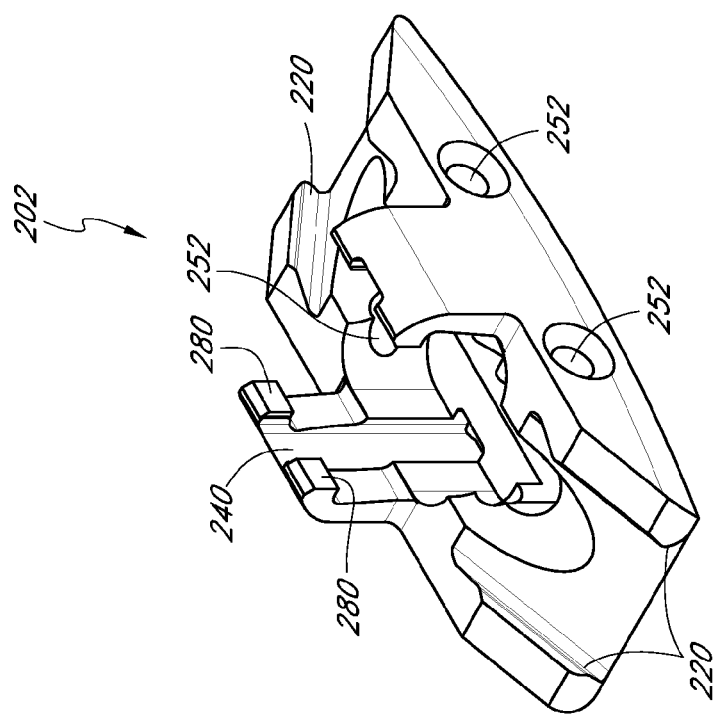
FIG. 21A is a bottom perspective view of an upper body portion of the intervertebral implant shown in FIG. 16A.

FIGS. 20A-B illustrate perspective views of the lower body portion 204 of the implant 200, according to an embodiment. These FIGS. provide additional clarity as to the configuration of the slots 222, the lower side portions 242, and the lower motion-limiting members 282 of the lower body portion 204. Similarly, FIGS. 21A-B illustrate perspective views of the upper body portion 202 of the implant 200, according to an embodiment. These FIGS. provide additional clarity as to the configuration of the slots 220, the upper side portions 240, and the upper motion-limiting members 280 of the upper body portion 202. Additionally, the upper and lower body portions 202, 204 can also define a central receptacle 290 wherein the actuator shaft can be received. Further, as mentioned above, the upper and lower body portions 202, 204 can define one or more apertures 252 to facilitate osseointegration.

Figure 22:
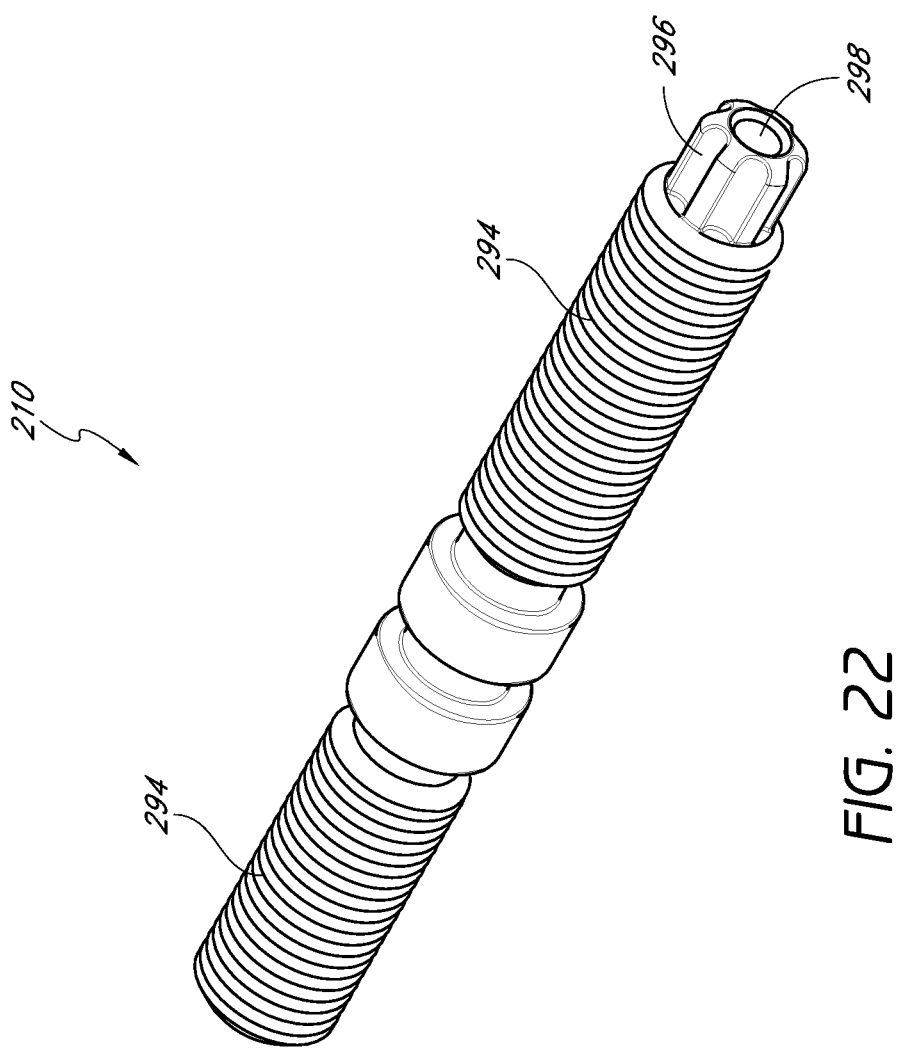
FIG. 22 is a perspective view of an actuator shaft of the intervertebral implant shown in FIG. 16A.

FIG. 22 is a perspective view of an actuator shaft 210 of the implant 200 shown in FIG. 16A. In this embodiment, the actuator shaft 210 can be a single, continuous component having threads 294 disposed thereon for engaging the proximal and distal wedge members 206, 208. The threads can be configured to be left hand threads at a distal end of the actuator shaft 210 and right hand threads at a proximal other end of the actuator shaft for engaging the respective ones of the distal and proximal wedge members 208, 206. Accordingly, upon rotation of the actuator shaft 210, the wedge members 206, 208 can be caused to move toward or away from each other to facilitate expansion or contraction of the implant 200. Further, as noted above, although this embodiment is described and illustrated as having the actuator shaft 210 with threads 294, it is also contemplated that relative movement of the wedge members can be achieved through the use of the actuator shaft 30 described in reference to FIGS. 5-6, and that such an actuator shaft could likewise be used with the embodiment shown in FIGS. 16A-19.

In accordance with an embodiment, the actuator shaft 210 can also comprise a tool engagement section 296 and a proximal engagement section 298. The tool engagement section 296 can be configured as a to be engaged by a tool, as described further below. The tool engagement section 296 can be shaped as a polygon, such as a hex shape. As shown, the tool engagement section 296 is star shaped and includes six points, which configuration tends to facilitate the transfer of torque to the actuator shaft 210 from the tool. Other shapes and configurations can also be used.

Furthermore, the proximal engagement section 298 of the actuator shaft 210 can comprise a threaded aperture. The threaded aperture can be used to engage a portion of the tool for temporarily connecting the tool to the implant 200. It is also contemplated that the proximal engagement section 298 can also engage with the tool via a snap or press fit.

Figure 23B:
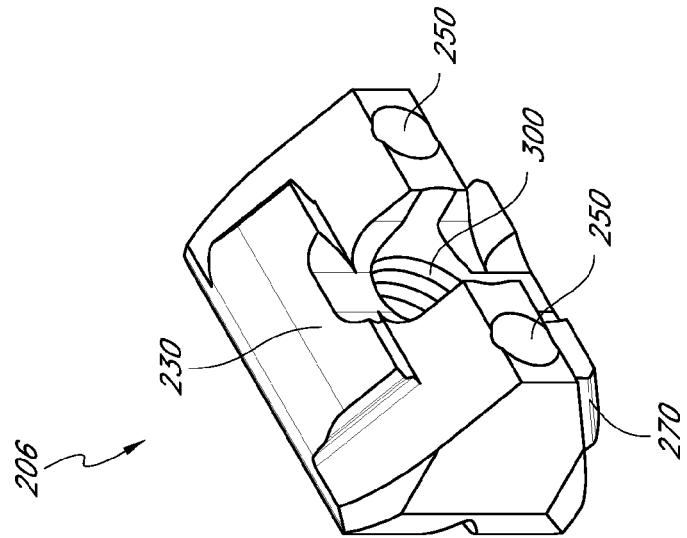
FIG. 23B is a rear perspective view of the proximal wedge member of the intervertebral implant shown in FIG. 16A.
Figure 23A:
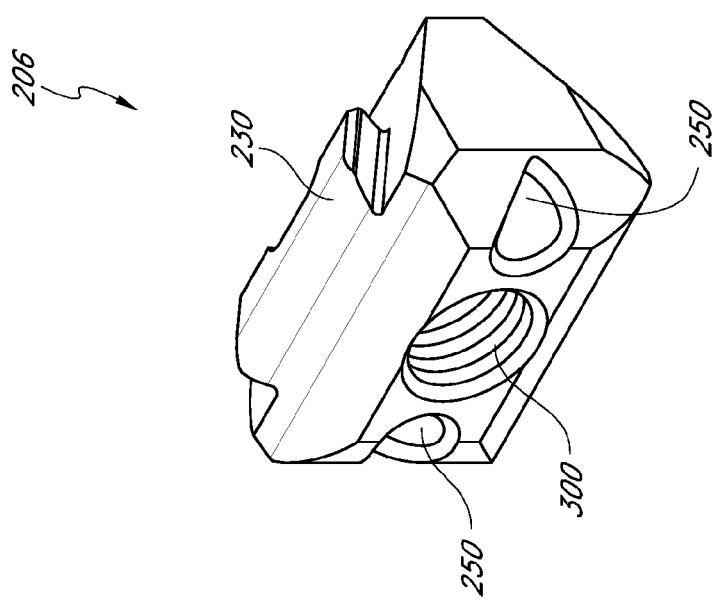
FIG. 23A is a front perspective view of a proximal wedge member of the intervertebral implant shown in FIG. 16A.

FIG. 23A-B illustrate perspective views of the proximal wedge member 206 of the implant 200. As described above, the proximal wedge member can include one or more anti-torque structures 250. Further, the guide members 230, 270 are also illustrated. The proximal wedge member 206 can comprise a central aperture 300 wherethrough an actuator shaft can be received. When actuator shaft 210 is used in an embodiment, the central aperture 300 can be threaded to correspond to the threads 294 of the actuator shaft 210. In other embodiments, the actuator shaft can engage other portions of the wedge member 206 for causing expansion or contraction thereof.

Figure 24B:
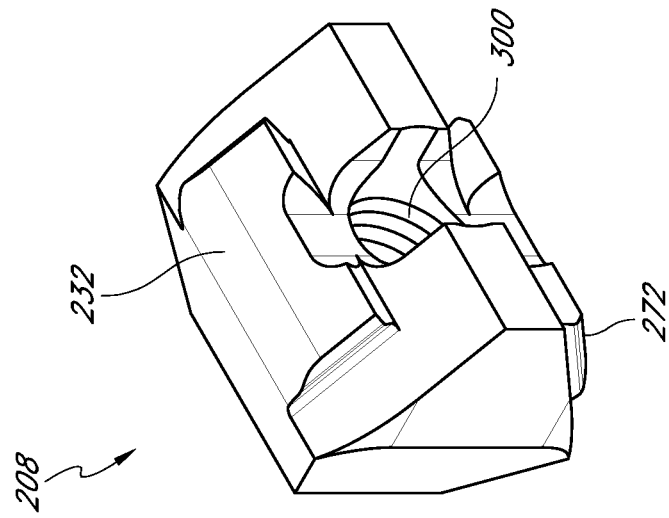
FIG. 24B is a rear perspective view of the distal wedge member of the intervertebral implant shown in FIG. 16A.
Figure 24A:
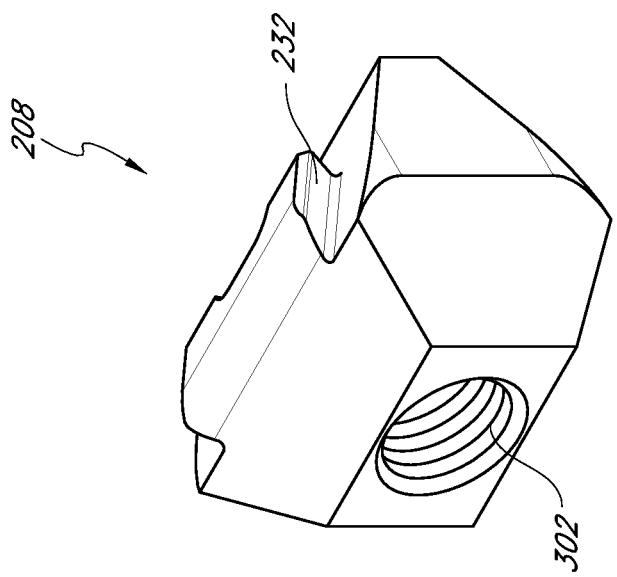
FIG. 24A is a front perspective view of a distal wedge member of the intervertebral implant shown in FIG. 16A.

FIG. 24A-B illustrate perspective views of the distal wedge member 208 of the implant 200. As similarly discussed above with respect to the proximal wedge member 206, the guide members 232, 272 and a central aperture 302 of the proximal wedge member 206 are illustrated. The central aperture 302 can be configured to receive an actuator shaft therethrough. When actuator shaft 210 is used in an embodiment, the central aperture 302 can be threaded to correspond to the threads 294 of the actuator shaft 210. In other embodiments, the actuator shaft can engage other portions of the wedge member 208 for causing expansion or contraction thereof.

Figure 25:
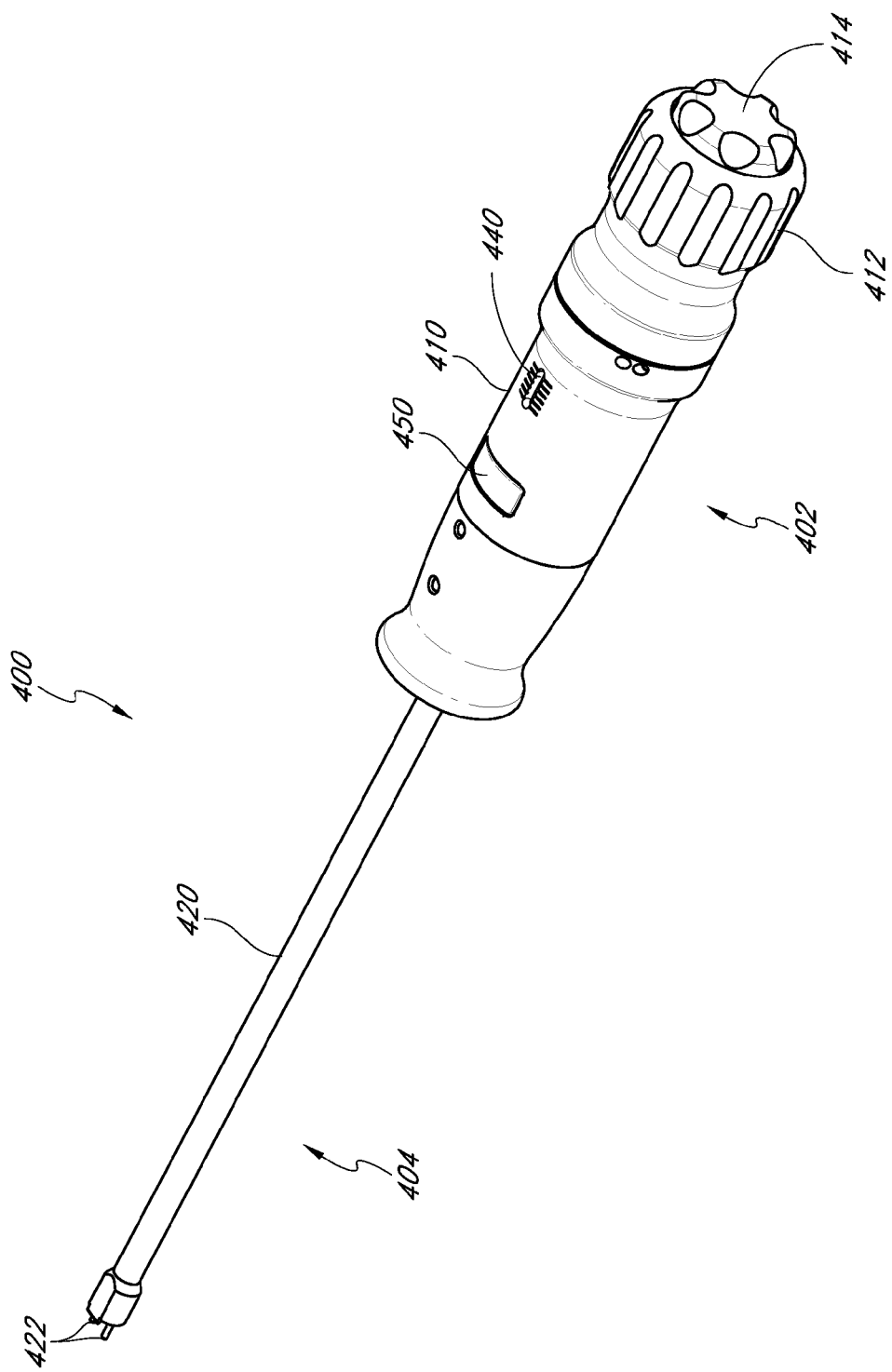
FIG. 25 is a perspective view of a deployment tool according to an embodiment.

Referring now to FIG. 25, there is illustrated a perspective view of a deployment tool 400 according to another embodiment. The tool 400 can comprise a handle section 402 and a distal engagement section 404. The handle portion 402 can be configured to be held by a user and can comprise various features to facilitate implantation and deployment of the implant.

According to an embodiment, the handle section 402 can comprise a fixed portion 410, and one or more rotatable portions, such as the rotatable deployment portion 412 and the rotatable teathering portion 414. In such an embodiment, the teathering portion 414 can be used to attach the implant to the tool 400 prior to insertion and deployment. The deployment portion 412 can be used to actuate the implant and rotate the actuator shaft thereof for expanding the implant. Then, after the implant is expanded and properly placed, the teathering portion 414 can again be used to unteather or decouple the implant from the tool 400.

Further, the distal engagement section 404 can comprise a fixed portion 420, an anti-torque component 422, a teathering rod (element 424 shown in FIG. 26), and a shaft actuator rod (element 426 shown in FIG. 26) to facilitate engagement with and actuation of the implant 200. The anti-torque component 422 can be coupled to the fixed portion 420. As described above with reference to FIGS. 16A-B, in an embodiment, the implant 200 can comprise one or more anti-torque structures 250. The anti-torque component 422 can comprise one or more protrusions that engage the anti-torque structures 250 to prevent movement of the implant 200 when a rotational force is applied to the actuator shaft 210 via the tool 400. As illustrated, the anti-torque component 422 can comprise a pair of pins that extend from a distal end of the tool 400. However, it is contemplated that the implant 200 and tool 400 can be variously configured such that the anti-torque structures 250 and the anti-torque component 422 interconnect to prevent a torque being transferred to the implant 200. The generation of the rotational force will be explained in greater detail below with reference to FIG. 26, which is a side-cross sectional view of the tool 400 illustrating the interrelationship of the components of the handle section 402 and the distal engagement section 404.

Figure 26:
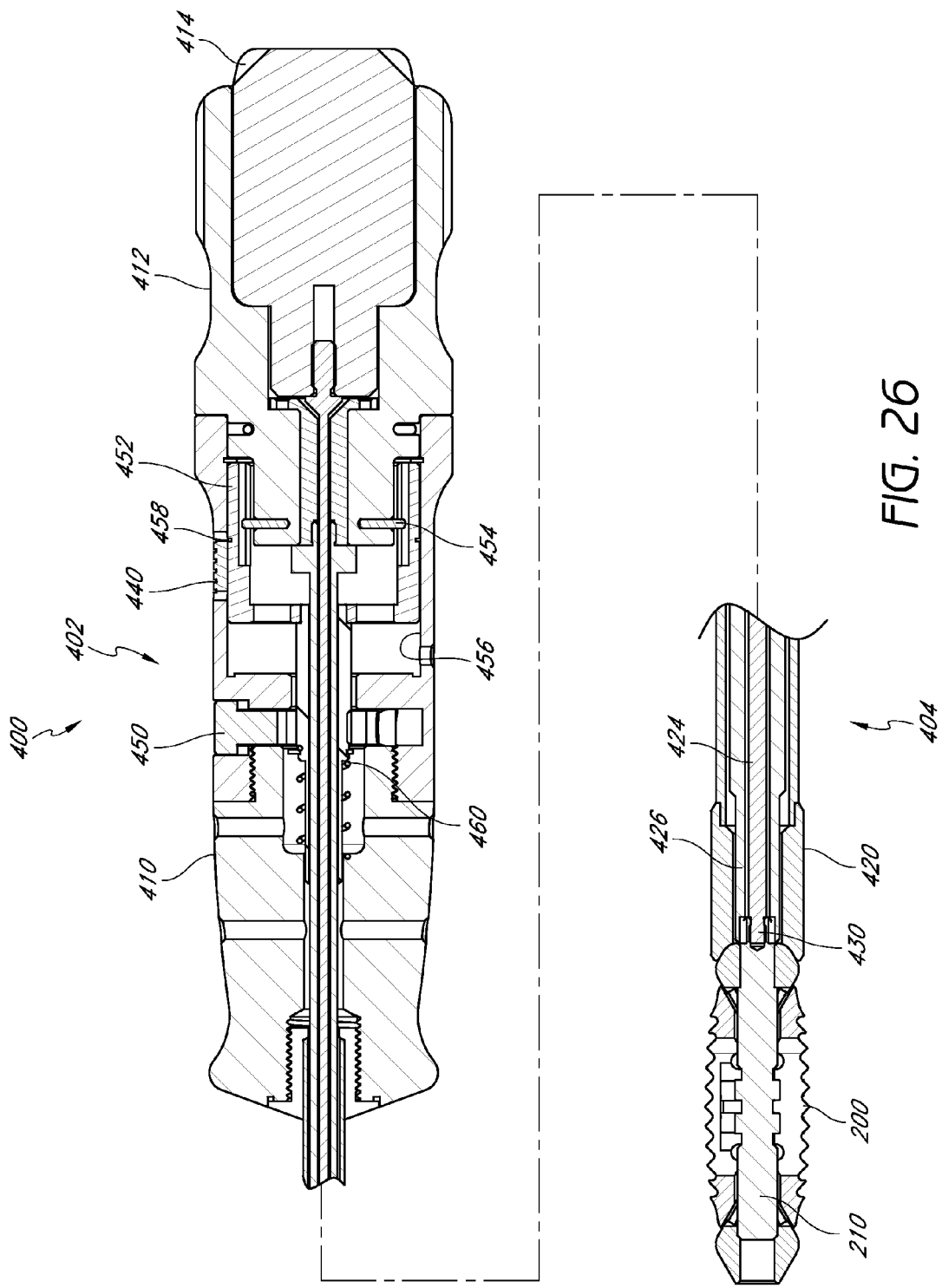
FIG. 26 is a side cross-sectional view of the deployment tool shown in FIG. 25 wherein an expandable implant is attached to a distal end thereof.

For example, as illustrated in FIG. 26, the fixed portion 410 of the handle section 402 can be interconnected with the fixed portion 420 of the distal engagement section 404. The distal engagement section 404 can be configured with the deployment portion 412 being coupled with the shaft actuator rod 426 and the teathering portion 414 being coupled with the teathering rod 424. Although these portions can be coupled to each other respectively, they can move independently of each other and independently of the fixed portions. Thus, while holding the fixed portion 410 of the handle section 402, the deployment portion 412 and the teathering portion 414 can be moved to selectively expand or contract the implant or to attach the implant to the tool, respectively. In the illustrated embodiment, these portions 412, 414 can be rotated to cause rotation of an actuator shaft 210 of an implant 200 engaged with the tool 400.

As shown in FIG. 26, the teather rod 424 can comprise a distal engagement member 430 being configured to engage a proximal end of the actuator shaft 210 of the implant 200 for rotating the actuator shaft 210 to thereby expand the implant from an unexpanded state to and expanded state. The teather rod 424 can be configured with the distal engagement member 430 being a threaded distal section of the rod 424 that can be threadably coupled to an interior threaded portion of the actuator shaft 210. As mentioned above, the anti-torque component 422 of the In some embodiments, the tool 400 can be prepared for a single-use and can be packaged with an implant preloaded onto the tool 400. This arrangement can facilitate the use of the implant and also provide a sterile implant and tool for an operation. Thus, the tool 400 can be disposable after use in deploying the implant.

Referring again to FIG. 25, an embodiment of the tool 400 can also comprise an expansion indicator gauge 440 and a reset button 450. The expansion indicator gauge 440 can be configured to provide a visual indication corresponding to the expansion of the implant 200. For example, the gauge 440 can illustrate an exact height of the implant 200 as it is expanded or the amount of expansion. As shown in FIG. 26, the tool 400 can comprise a centrally disposed slider element 452 that can be in threaded engagement with a thread component 454 coupled to the deployment portion 412.

In an embodiment, the slider element 452 and an internal cavity 456 of the tool can be configured such that the slider element 452 is provided only translational movement in the longitudinal direction of the tool 400. Accordingly, as the deployment portion 412 is rotated, the thread component 454 is also rotated. In such an embodiment, as the thread component 454 rotates and is in engagement with the slider component 452, the slider element 452 can be incrementally moved from an initial position within the cavity 456 in response to the rotation of the deployment portion 412. An indicator 458 can thus be longitudinally moved and viewed to allow the gauge 440 to visually indicate the expansion and/or height of the implant 200. In such an embodiment, the gauge 440 can comprises a transparent window through which the indicator 458 on the slider element 452 can be seen. In the illustrated embodiment, the indicator 458 can be a marking on an exterior surface of the slider element 452.

In embodiments where the tool 400 can be reused, the reset button 450 can be utilized to zero out the gauge 440 to a pre-expansion setting. In such an embodiment, the slider element 452 can be spring-loaded, as shown with the spring 460 in FIG. 26. The reset button 450 can disengage the slider element 452 and the thread component 454 to allow the slider element 452 to be forced back to the initial position.

The specific dimensions of any of the embodiment disclosed herein can be readily varied depending upon the intended application, as will be apparent to those of skill in the art in view of the disclosure herein. Moreover, although the present inventions have been described in terms of certain preferred embodiments, other embodiments of the inventions including variations in the number of parts, dimensions, configuration and materials will be apparent to those of skill in the art in view of the disclosure herein. In addition, all features discussed in connection with any one embodiment herein can be readily adapted for use in other embodiments herein to form various combinations and sub-combinations.

The use of different terms or reference numerals for similar features in different embodiments does not imply differences other than those which may be expressly set forth. Accordingly, the present inventions are intended to be described solely by reference to the appended claims, and not limited to the preferred embodiments disclosed herein.

What is claimed is:

1. A method of implanting an expandable intervertebral implant comprising:

positioning the implant between two vertebral bodies via a transforaminal approach, wherein the implant comprises:

upper and lower body portions each having proximal and distal surfaces at proximal and distal ends thereof, the proximal and distal surfaces of the upper and lower body portions generally facing each other;

an actuator shaft received between the upper and lower body portions, the actuator shaft comprising an inner member and an outer sleeve member moveable relative to the inner member, the inner member having distal and proximal ends and at least one retention structure disposed therebetween, the outer sleeve member having a proximal end and at least one complementary retention structure to engage the retention structure of the inner member to facilitate selective relative movement of the proximal end of the outer sleeve member toward the distal end of the inner member;

a proximal wedge member disposed at the proximal end of the outer sleeve member; and a distal wedge member disposed at the distal end of the inner member; and moving the inner member of the actuator shaft in an proximal direction relative to the outer sleeve member to force the proximal wedge member against the proximal surfaces of the upper and lower body portions, and to force the distal wedge member against the distal surfaces of the upper and lower body portions, expanding implant the implant.

2. The method of claim 1, wherein moving the inner member of the actuator shaft comprises rotating the inner member.

3. The method of claim 1, wherein moving the inner member of the actuator shaft comprises laterally advancing the actuator shaft without rotation.

4. The method of claim 1, wherein the proximal wedge member includes an engagement surface and the proximal surfaces of the upper and lower body portions include complementary engagement surfaces configured to engage the engagement surface of the proximal wedge member, such that forcing the proximal wedge member against the proximal surfaces of the upper and lower body portions results in one-way longitudinal movement of the proximal wedge member relative to the proximal surfaces of the upper and lower body portions.

5. The method of claim 4, wherein the one-way longitudinal movement maintains the upper and lower body portions at a given separation distance.

6. The method of claim 1, wherein the distal wedge member includes an engagement surface and the distal surfaces of the upper and lower body portions include complementary engagement surfaces configured to engage the engagement surface of the distal wedge member, such that forcing the distal wedge member against the proximal surfaces of the upper and lower body portions results in one-way longitudinal movement of the distal wedge member relative to the distal surfaces of the upper and lower body portions.

7. The method of claim 6, wherein the one-way longitudinal movement maintains the upper and lower body portions at a given separation distance.

8. The method of claim 1, wherein the implant further comprises an alignment guide extending at least partially through the upper and lower body portions.

9. The method of claim 8, wherein the alignment guide restricts the expanding of the implant to occur in a direction substantially orthogonal to an axis of the actuator shaft.

* * * * *

UNITED STATES PATENT AND TRADEMARK OFFICE
CERTIFICATE OF CORRECTION

PATENT NO.        : 8,568,481 B2                                    Page 1 of 1
APPLICATION NO.   : 13/334526
DATED             : October 29, 2013
INVENTOR(S)       : Olmos et al.

It is certified that error appears in the above-identified patent and that said Letters Patent is hereby corrected as shown below:

In the Specification

In column 7 at lines 26-27, Change "veterbal" to --vertebral--.

In column 7 at line 38, Change "posterial" to --posterior--.

In column 8 at line 29, Change "diskectomy." to --discectomy--.

In column 26 at line 47, Change "as a to be" to --as to be--.

In column 28 at lines 14-15, Delete "As mentioned above, the anti-torque component 422 of the".

In the Claims

In column 29, at lines 38-39, In Claim 1, Change "expanding implant the implant" to --expanding the implant--.

Signed and Sealed this
Third Day of June, 2014

Michelle K. Lee
*Deputy Director of the United States Patent and Trademark Office*